(12) United States Patent
Dorsch et al.

(10) Patent No.: US 6,960,599 B2
(45) Date of Patent: Nov. 1, 2005

(54) HETEROCYCLIC AMINOALKYLPYRIDINE DERIVATIVES AS PSYCHOPHARMACEUTICALS

(75) Inventors: Dieter Dorsch, Ober-Ramstadt (DE); Henning Boettcher, Darmstadt (DE); Michael Arlt, Seeheim (DE); Christoph Seyfried, Seeheim-Jugenheim (DE); Gerd Bartoszyk, Weiterstadt (DE); Juergen Harting, Darmstadt (DE); Rudolf Gottschlich, Reinheim (DE)

(73) Assignee: Merck Patent GmbH, Darmstadt (DE)

( * ) Notice: Subject to any disclaimer, the term of this patent is extended or adjusted under 35 U.S.C. 154(b) by 16 days.

(21) Appl. No.: 10/311,286

(22) PCT Filed: Jun. 19, 2001

(86) PCT No.: PCT/EP01/06915
§ 371 (c)(1),
(2), (4) Date: Jul. 21, 2003

(87) PCT Pub. No.: WO01/98293
PCT Pub. Date: Dec. 27, 2001

(65) Prior Publication Data
US 2004/0019044 A1 Jan. 29, 2004

(30) Foreign Application Priority Data
Jun. 20, 2000 (DE) .......................... 100 29 371

(51) Int. Cl.$^7$ ..................... C07D 401/02; A61K 31/44; A61K 31/47
(52) U.S. Cl. ................... 514/307; 514/311; 514/332; 514/336; 514/338; 546/148; 546/152; 546/255; 546/268.1; 546/270.1
(58) Field of Search .................. 514/307, 311, 514/332, 336, 338, 357; 546/148, 152, 255, 268.1, 270, 333

(56) References Cited
U.S. PATENT DOCUMENTS

| | | |
|---|---|---|
| 4,983,586 A | 1/1991 | Bodor |
| 5,177,088 A | 1/1993 | Effland et al. |
| 5,767,132 A | 6/1998 | Bottcher et al. |

FOREIGN PATENT DOCUMENTS

| | | |
|---|---|---|
| EP | 0 509 402 A1 | 10/1992 |
| EP | 0 707 007 A1 | 4/1996 |

Primary Examiner—Zinna Northington Davis
(74) Attorney, Agent, or Firm—Millen White Zelano & Branigan, P.C.

(57) ABSTRACT

The invention relates to heterocyclic aminoalkylpyridine derivatives of the formula I:

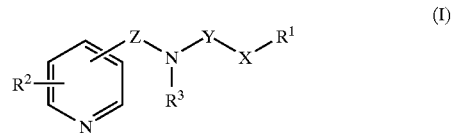

where
$R^1$ is the radical of a heterocycle having 1 to 3 ring structures, where each ring structure is saturated, unsaturated or aromatic and optionally fused to other ring structures to give a fused ring system and the heterocycle has a total of 1 to 4 N, O and/or S atoms in the ring structures and is optionally monosubstituted, disubstituted or trisubstituted by one or more of the groups -A, —$OR^4$, —$N(R^4)_2$, —$NO_2$, —CN, Hal, —$COOR^4$, —$CON(R^4)_2$, —$COR^4$, =O;
$R^2$ is a phenyl group which is optionally monosubstituted, disubstituted, trisubstituted, tetrasubstituted or pentasubstituted by one or more of the groups Hal, -A, —O-A, —$NO_2$ or —CN,
or is a thienyl group which is optionally monosubstituted or disubstituted by one or more of the groups Hal, -A, —O-A, -$NO_2$, —CN or thienyl;
$R^3$ is H, -A, —CO-A, —$C(R^4)_2R^2$, —$C(R^4)_2$-pyridinediyl-$R^2$;
$R^4$ is H or -A;
A is $C_1$-$C_6$-alkyl, where 1 to 7 hydrogen atoms are optionally replaced by fluorine;
—X— is —O—, —S—, sulfinyl, sulfonyl, —$C(R^4)_2$—;
—Y— is —$[C(R^4)_2]_n$—;
—Z— is —$C(R^4)_2$—;
Hal is F, Cl, Br or I;
n is 1, 2, 3 or 4;
and their tolerable salts and solvates and their use as medicaments.

17 Claims, No Drawings

HETEROCYCLIC AMINOALKYLPYRIDINE DERIVATIVES AS PSYCHOPHARMACEUTICALS

The invention relates to heterocyclic aminoalkylpyridine derivatives, their preparation and their use as psychopharmaceuticals.

The heterocyclic aminoalkylpyridine derivatives can be represented by the general formula I:

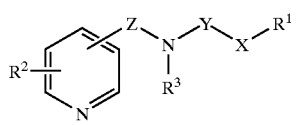

(I)

where $R^1$ is the radical of a heterocycle having 1 to 3 ring structures, where each ring structure is saturated, unsaturated or aromatic and optionally fused to other ring structures to give a fused ring system and the heterocycle has a total of 1 to 4 N, O and/or S atoms in the ring structures and is optionally monosubstituted, disubstituted or trisubstituted by one or more of the groups -A, $-OR^4$, $-N(R^4)_2$, $-NO_2$, $-CN$, Hal, $-COOR^4$, $-CON(R^4)_2$, $-COR^4$, $=O$;

$R^2$ is a phenyl group which is optionally monosubstituted, disubstituted, trisubstituted, tetrasubstituted or pentasubstituted by one or more of the groups Hal, -A, —O-A, $-NO_2$ or $-CN$, or is a thienyl group which is optionally monosubstituted or disubstituted by one or more of the groups Hal, -A, —O-A, $-NO_2$, $-CN$ or thienyl;

$R^3$ is H, -A, —CO-A, $-C(R^4)_2R^2$, $-C(R^4)_2$-pyridinediyl-$R^2$;

$R^4$ is H or -A;

A is $C_1-C_6$-alkyl, where 1 to 7 hydrogen atoms are optionally replaced by fluorine;

—X— is —O—, —S—, sulfinyl, sulfonyl, $-C(R^4)_2-$;

—Y— is $-[C(R^4)_2]_n-$;

—Z— is $-C(R^4)_2-$;

Hal is F, Cl, Br or I;

n is 1, 2, 3 or 4;

and their tolerable salts and solvates.

Psychoses, which also include diseases of the schizophrenia type, have been attributed to a hyperactivity of the limbic dopamine system (Snyder et al., Science 184: 1243–1253, 1974). The antipsychotic effect of neuroleptics has been attributed to their $D_2$-antagonistic properties (with regard to the nomenclature of the receptors: Basic Neurochemistry, Editors: G. J. Siegel, B. W. Agranoff, R. W. Albers, P. B. Molinoff, 5th edition, Raven Press, Ltd., N. Y. USA, Chapters 12 and 13; otherwise the following technical publications: Creese et al., Science 192: 481–483, 1976; Farde et al., Psychopharmacology 99: 28–31, 1989; Feeman et al., Nature 261: 717–719, 1976; Wiesel et al., Prog. Neuro-Psychopharmacol. & Biol. Psychiat. 14: 759–767, 1990). Consequently, the classical dopamine hypothesis of schizophrenia was formulated, according to which neuroleptics have to bind to the $D_2$ receptor. On account of their extrapyramidal side effects, the employment of classical $D_2$ antagonists is severely restricted, especially in the case of chronic administration. The extrapyramidal side effects include, for example, tremor, akinesia, dystonia and akathisia (Cavallaro & Smeraldi, CNS Drugs 4: 278–293, 1995). There are only a few antipsychotics which cause significantly fewer or no extrapyramidal side effects at all and which are described as "atypical neuroleptics" (Kervin, Brit. J. Psychiatry 1964, 141–148, 1994). The prototype atypical neuroleptic clozapine has extremely low extrapyramidal side effects, but causes other serious complications such as agranulocytosis, which sometimes is fatal (Alvir et al., New Engl. J. Med. 329: 162–167, 1993).

Because $5\text{-HT}_{1A}$ agonists intensify antipsychotic properties of conventional dopamine $D_2$ antagonists in animals (Wadenberg & Ahlenios, J. Neural. Transm. 74: 195–198, 1988) and prevent the catalepsy induced by dopamine $D_2$ antagonists (Costall et al., Neuropharmacology 14: 859–868, 1975), $5\text{-HT}_{1A}$-agonistic properties could be advantageous. The efficacy of buspirone, a pharmacon having $5\text{-HT}_{1A}$-agonistic and dopamine $D_2$-antagonistic properties, has been demonstrated in schizophrenia patients (Goff et al., J. Clin, Psychopharmacol. 11: 193–197, 1991). Apart from various dopamine autoreceptor agonists which also have a significant affinity for the $5\text{-HT}_{1A}$ receptor (e.g. U-86170F, Lahti et al., Naunyn-Schmiedeberg's Arch. Pharmacol. 344: 509–513, 1991), PD1431188 (Melzer et al., J. Pharmacol. Exp. Ther. 274: 912–920, 1995) and roxindole (Bartoszyk et al., J. Pharmacol., Exp. Ther. 276: 41–48, 1996), only a few dopamine $D_2$ antagonists have been developed which also have an affinity for the $5\text{-HT}_{1A}$ receptor, such as mazapertine (Reiz et al., J. Mid. Chem. 37: 1060–1062, 1994), S16924 (Millan et al., Br. J. Pharmacol. 114: 156 B, 1995) or ziprasidone (Seeger et al., J. Pharmacol. Exp. Ther. 275: 101–113, 1995). These already known compounds have disadvantages with respect to affinity or specificity. Thus mazapertine also shows an affinity for the $\alpha_1$ receptor. S16924 additionally has $5\text{-HT}_{2A/C}$-antagonistic properties and ziprasidone moreover binds to the $5\text{-HT}_{1D/2A/2C}$ receptors.

It is the object of the invention to make available medicaments, in particular psychopharmaceuticals. It is a further object of the invention to make available compounds which bind both to the dopamine $D_2$ receptor and to the $5\text{-HT}_{1A}$ receptor.

This object is achieved by the compounds of the general formula I and by their tolerable salts and solvates (see above).

Their binding properties can be determined by known $5\text{-HT}_{1A}$ (serotonin) binding test and dopamine binding tests ($5\text{-HT}_{1A}$ (serotonin) binding test: Matzen et al., J. Med. Chem., 43, 1149–1157, (2000) in particular page 1156 with reference to Eur. J. Pharmacol.: 140, 143–155 (1987); dopamine binding tests: Böttcher et al., J. Med. Chem.: 35, 4020–4026, (1992) with reference to J. Neurochem.: 46, 1058–1067 (1986)).

These compounds differ both from the aforementioned atypical neuroleptics and from the amino(thio)ethers disclosed in EP-A 0 707 007, of the formula:

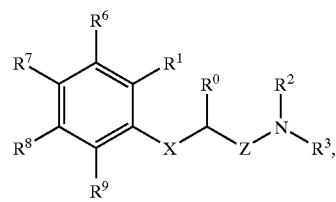

where $R^0$ to $R^9$, X and Z have the meanings defined in EP-A 0 707 007.

The compounds according to the invention can be employed for the treatment of diseases which are associated with the serotonin and dopamine neurotransmitter system and in which high-affinity serotinin receptors ($5\text{-HT}_{1A}$ receptors) and/or dopamine $D_2$ receptors are involved. The most important indication for the administration of the compound of the general formula I are psychoses of any type, in particular also mental disorders of the schizophrenia type. Moreover, the compounds can also be employed for the prevention of cognitive functional disorders, i.e. for improvement of the learning ability and of the memory. The compounds of the general formula I are also suitable for the control of the symptoms of Alzheimer's disease. The substances of the general formula I according to the invention are moreover suitable for the prophylaxis and control of cerebral infarcts (cerebral apoplexy), such as cerebral stroke and cerebral ischemia. The substances are also suitable for the treatment of disorders such as pathological anxiety states, overexcitation, hyperactivity and attention disorders in children and adolescents, deep-seated developmental disorders and disorders of social behavior with mental retardation, depression, compulsive disorders in the narrower (OCD) and wider sense (OCSD), certain sexual function disorders, sleep disorders and eating disorders, and also such psychiatric symptoms in the context of senile dementia and dementia of the Alzheimer type, i.e. diseases of the central nervous system in the widest sense.

The compounds of the general formula I and their tolerable salts and solvates can thus be employed as active ingredients of medicaments such as anxiolytics, antidepressants, neuroleptics and/or antihypertensives.

$R^1$ is an optionally substituted heterocycle having 1 to 3 ring structures. The number of ring structures of a heterocycle is identical to the number of ring openings which imaginarily have to be carried out in order to convert the heterocycle into an acyclic compound. The ring structures can be independent of one another, if that is chemically possible, saturated, unsaturated or aromatic. A ring structure can optionally be fused to other ring structures to give a fused ring system. Nonaromatic saturated or unsaturated ring structures can also be connected to one another in analogy to fused ring systems, that is share bonds with one another, as is the case, for example, with steroids or with chroman. The heterocycle comprises a total of 1 to 4 nitrogen, oxygen and/or sulfur atoms, which replace the carbon atoms in the ring structures. Preferably, these N, O and/or S atoms are not adjacent. The heterocycle is optionally monosubstituted, disubstituted or trisubstituted by one or more of the groups -A, $—OR^4$, $N(R^4)_2$, $—NO_2$, $—CN$, Hal, $—COOR^4$, $—CON(R^4)_2$, $—COR^4$, $=O$. $R^1$ is preferably quinolyl, isoquinolyl, which optionally has at least one chlorine substituent, or indolyl, benzothiazolyl, coumaronyl, coumarinyl, pyridyl or carbazolyl, where optionally at least one hydrogen of the quinolyl, isoquinolyl, indolyl or benzothiazolyl is replaced by a methyl group or ethoxycarbonyl group. In particular, $R^1$ carries the meaning quinolin-7-yl, quinolin-8-yl, where a hydrogen is optionally replaced by a chlorine atom in position 5, or indol-4-yl or indol-7-yl, where a hydrogen in position 2 of the quinolyl or indolyl is optionally replaced by a methyl group or ethoxycarbonyl group. The meanings indol-4-yl, 2-methylindol-4-yl and quinolin-8-yl are particularly preferred for $R^1$.

$R^2$ is a phenyl group which is optionally monosubstituted, disubstituted, trisubstituted, tetrasubstituted or pentasubstituted by one or more groups Hal, -A, $—O-A-$, $—NO_2$ or $—CN—R^2$ can further carry the meaning of a thienyl group which is optionally monosubstituted or disubstituted by one or more of the groups Hal, -A, $—O-A-$, $NO_2$, $—CN$ or thienyl. $R^2$ is preferably fluorophenyl, difluorophenyl, cyanophenyl or tolyl. In particular, $R^2$ has the meaning fluorophenyl, 2,4-difluorophenyl, 3-cyanophenyl or 4-methylphenyl.

$R^3$ carries the meaning H, -A, $—CO-A-$, $—C(R^4)_2R^2$, $—C(R^4)_2$-pyridinediyl-$R^2$:

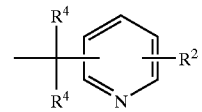

The meaning $R^3$ equal to H is preferred.
$R^4$ carries the meaning H or -A, where H is preferred.
A is $C_1$–$C_6$-alkyl, where 1 to 7 hydrogen atoms are optionally replaced by fluorine. A can be branched or unbranched and is preferably methyl, ethyl, propyl, isopropyl, n-butyl, sec-butyl, tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl. Methyl, ethyl, isopropyl, n-propyl, n-butyl or tert-butyl is particularly preferred for A.
$—X—$ can assume the meaning $—O—$, $—S—$, sulfinyl, sulfonyl or $—C(R^4)_2—$, where the meaning oxygen ($—O—$) is preferred.
$—Y—$ is $—[C(R^4)_2]_n—$, in particular ethylene ($—CH_2—CH_2—$).
$—Z—$ has the meaning $—C(R^4)_2—$, in particular methylene ($—CH_2—$).
Hal is F, Cl, Br or I where F and Cl, in particular F, are preferred.
n is 1, 2, 3 or 4, where n equal to 2 is preferred.

The substituents $R^1$, $R^2$, $R^3$, X, Y, Z can independently of one another assume one of the aforementioned meanings. If, in $R^1$, $R^2$, $R^3$, X, Y, Z, the meaning of one of the terms assumes substituents containing $R^4$, A, Hal or n, $R^4$, A, Hal and n can have another meaning in any substituent $R^1$, $R^2$, $R^3$, X, Y, Z. The compounds of the general formula I are all the more highly preferred, the more their substituents have preferred meanings and the more highly these meanings are preferred.

A preferred compound of the general formula I is described by the general formula VIII, where Z is methylene, Y is ethylene, $R^3$ is H and X is oxygen and Z and X are in the meta-position relative to the pyridine nitrogen:

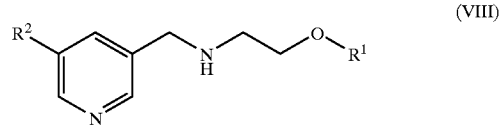

(VIII)

If the compounds of the general formula I are optically active, the formula I includes both any isolated optical antipodes and the corresponding optionally racemic mixtures in any conceivable composition.

A compound of the general formula I can be converted into the corresponding salt (that is acid addition salt) using an acid. Acids which afford the tolerable (that is biocompatible and adequately bioavailable) salts are suitable for this reaction. It is thus possible to use inorganic acids such as sulfuric acid or hydrohalic acids such as hydrochloric acid, bromic acid or phosphoric acids such as orthophosphoric acid, nitric acid, sulfamic acid, aliphatic, alicyclic, araliphatic, aromatic or heterocyclic monobasic or polybasic carboxylic acids, sulfonic acids or sulfuric acid derivatives such as formic acid, acetic acid, pronionic acid, pivalic acid diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methanesulfonic acid or ethanesulfonic acid, ethanedisulfonic acid, 2-hydroxyethanesulfonic acid, benzenesulfonic acid, paratoluenesulfonic acid, naphthalenemonosulfonic acid and naphthalenedisulfonic acid and sulfuric acid lauryl ester.

If desired, the corresponding free bases of the general formula I can be liberated by the treatment of their salts with strong bases such as sodium hydroxide, potassium hydroxide or sodium or potassium carbonate, provided that no other acidic groups are present in the molecule. In the last-mentioned cases, in which the compounds of the general formula I carry free acidic groups, salt formation can also be brought about by treatment with strong bases. Suitable bases are alkali metal hydroxides, alkaline earth metal hydroxides, or organic bases in the form of primary, secondary or tertiary amines.

Solvates of the compounds of the general formula I are understood as meaning adducts of chemically "inert" solvent molecules to the compounds of the formula I which are formed on account of their mutual attractive force. Solvates are, for example, mono- and dihydrates or addition compounds with alcohols such as methanol or ethanol.

It is known that pharmaceuticals can be converted synthetically into derivatives (for example into alkyl or acyl derivatives, into sugar or oligopeptide derivatives and others) which are converted back into the active compounds of the general formula I in the body metabolically by extracellular or intracellular enzymes. The invention also relates to such "prodrug derivatives" of the compounds of the general formula I.

A further subject of the invention is the use of a compound of the general formula I or of one of its tolerable salts or solvates for the production of a medicament which is suitable for the treatment of human or animal disorders, in particular of disorders of the central nervous system such as pathological anxiety states, depression and/or psychoses, for the prevention of side effects during the treatment of high blood pressure (e.g. with α-methyldopa), for the treatment of endocrinological and/or gynecological disorders, e.g. for the treatment of acromegaly, hypogonadism, secondary amenorrhea, the post-menstrual syndrome and undesired lactation in puberty and for the prophylaxis and therapy of cerebral disorders (e.g. of migraine), in particular in geriatrics, in a similar manner to specific ergot alkaloids and for the control and prophylaxis of cerebral infarct (cerebral apoplexy) such as cerebral stroke and cerebral ischemia. Moreover, the pharmaceutical preparations and medicaments which contain a compound of the general formula I are suitable for improvement of the cognitive functional ability and for the treatment of Alzheimer's disease symptoms. In particular, such medicaments are suitable for the treatment of mental disorders of the schizophrenia type and for the control of psychotic anxiety states. The term treatment in the context of the invention includes prophylaxis and therapy of human or animal diseases.

The substances of the general formula I are normally administered analogously to known, commercially obtainable pharmaceutical preparations (e.g. of bromocriptine and dihydroergocornine), preferably in doses of between 0.2 and 500 mg, in particular of between 0.2 and 15 mg per dose unit. The daily dose unit is between 0.001 and 10 mg per kg of body weight. Low doses (of between 0.2 and 1 mg per dose unit, 0.001 to 0.005 mg per kg of body weight) are particularly suitable for pharmaceutical preparations for the treatment of migraine. A dose of between 10 and 50 mg per dose unit is preferred for other indications. However, the dose to be administered depends on a large number of factors, e.g. on the efficacy of the corresponding component, the age, the body weight and the general condition of the patient.

A further subject of the invention is a process for the production of a pharmaceutical preparation, which comprises the conversion of a compound of the general formula I or of one of its tolerable salts or solvates to a suitable dose form together with a suitable vehicle. The compounds of the general formula I can be brought into a suitable dose form together with at least one vehicle or excipient, if appropriate in combination with a further active ingredient.

Suitable vehicles are organic or inorganic substances which are suitable for enteral (e.g. oral) or parenteral or topical administration and which do not react with the substances of the general formula I according to the invention. Examples of such vehicles are water, vegetable oils, benzyl alcohols, polyethylene glycols, gelatin, carbohydrates such as lactose and starch, magnesium stearate, talc and raw petroleum jelly. Tablets, coated tablets, capsules, syrups, juices, drops or suppositories are in particular employed for enteral administration. Solutions, preferably oily or aqueous solutions, such as suspensions, emulsions or alternatively implants are used for parenteral administration. Ointments, creams or powders are employed in the case of external application. The compounds of the general formula I can also be lyophilized and the resulting lyophilizates processed to give injectable preparations.

The invention further relates to medicaments which contain at least one compound of the general formula I or one of its tolerable salts or solvates and, if appropriate, further ingredients such as vehicles, excipients etc. These preparations can be employed as medicaments for the treatment of human or animal diseases.

The aforementioned medicaments can be sterilized and processed together with excipients such as lubricants, preservatives, stabilizers and/or wetting agents, emulsifiers, osmotically active substances, buffers, colorants or flavor enhancers to give other pharmaceutical preparations.

A further subject of the invention is a process for the preparation of the compounds of the general formula I. This process is suitable for compounds in which the substituent Z is in the meta-position relative to the nitrogen of the pyridine ring connected to Z and in which Z has the meaning of methylene.

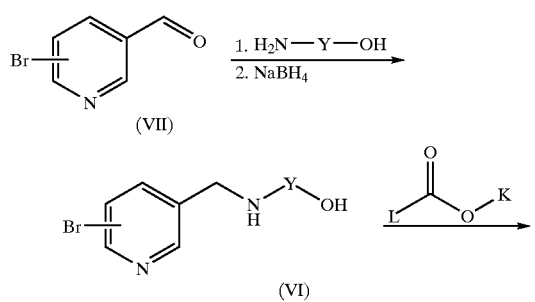

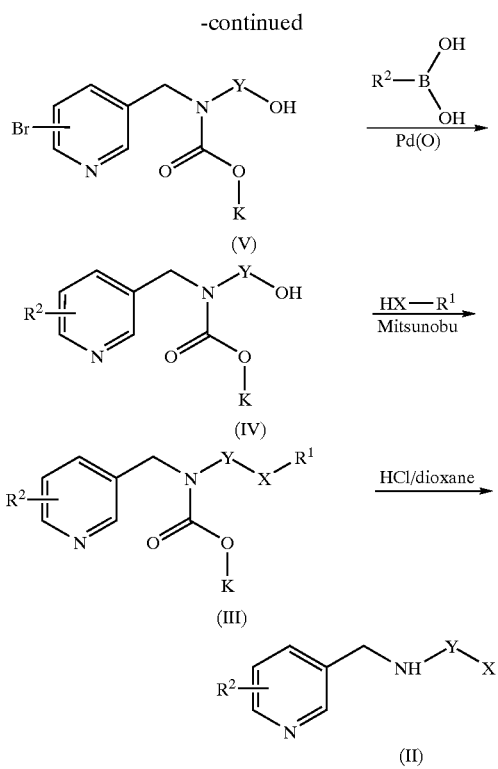

In a first step, bromopyridin-3-ylmethanal (VII) is reacted with $H_2N$—Y—OH and, for example, sodium borohydride to give a compound of the general formula VI. In a second step, the secondary amine of the general formula VI is provided with a protective group. This is carried out with addition of reagents of the formula L-CO—O—K, where K has the meaning of tert-butyl, fluoren-9-ylmethyl or benzyl and L is either Cl, $N_3$ or tert-butoxycarbonyloxy. Compounds of the general formula V are reacted with suitable boronic acid derivatives ($R^2$—$B(OH)_2$) using an appropriate Pd(0) catalyst, compounds of the formula IV resulting in which the bromine atom is replaced by the $R^2$ substituent (Suzuki coupling, cf. A. Suzuki, N. Miyaura Chem. Rev. 1995, 95, 2457–2483; A. R. Martin, Y. Yang, Acta Chem. Scand. 1993, 47, 221–230). With the aid of the Mitsunobu reaction, compounds of the general formula IV are reacted with compounds of the formula HX—$R^1$, compounds of the formula III resulting. Details of the named reaction can be taken from: Mitsunobu, Bull. Chem. Soc. Jpn.: 40, 4235–4238 (1967); Hughes, Org. React.: 42, 335–656 (1992); Mitsunobu, Synthesis, 1–28 (1981); Hughes et al., J. Am. Chem. Soc.: 110, 6487–6491 (1988); Crich et al., J. Org. Chem.: 54, 257–259 (1989); Camp et al., J. Org. Chem.: 54, 3045–3049, 3049–3054 (1989). The protective group is then removed from compounds of the general formula III, compounds of the general formula II resulting. By means of alkylation reactions known to the person skilled in the art, substituents $R^3$ can be introduced into compounds of the general formula II.

Alternatively, the synthesis is carried out via the following intermediates:

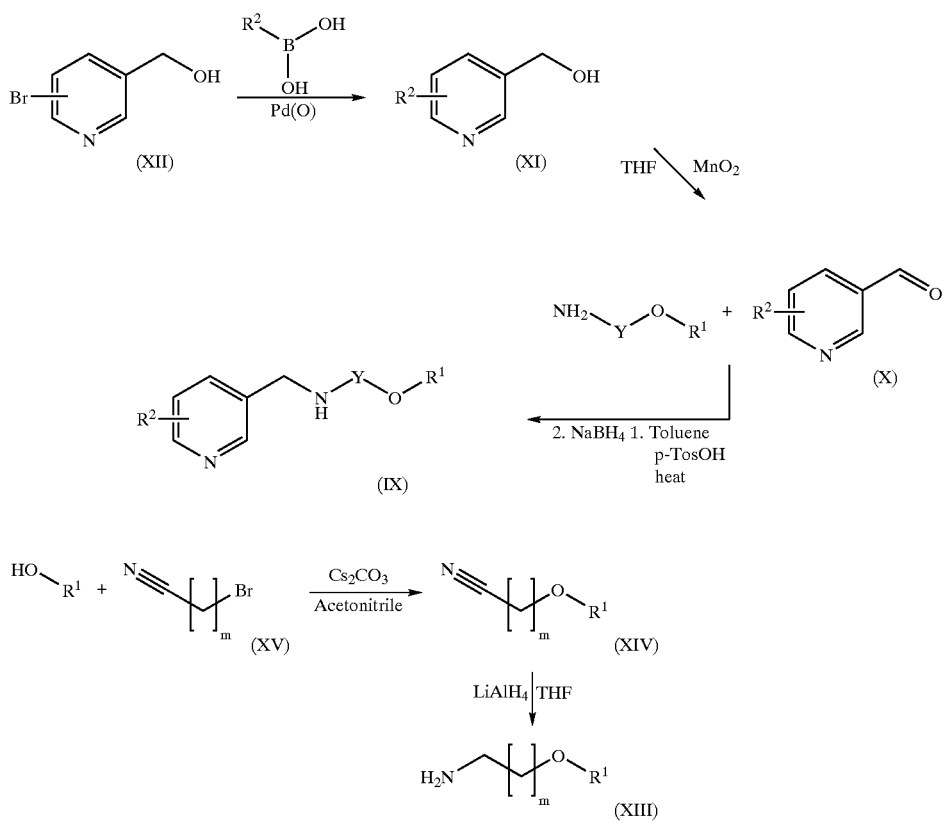

The invention likewise relates to this alternative process. By means of the Suzuki reaction, a bromopyridylmethanol of the formula XII is coupled to a boronic acid derivative $R^2$—$B(OH)_2$ under Pd(0) catalysis (Suzuki coupling, cf. A. Suzuki, N. Miyaura Chem. Rev. 1995, 95, 2457–2483; A. R. Martin, Y. Yang, Acta Chem. Scand. 1993, 47, 221–230). The alcohol of the formula XI resulting here is oxidized, e.g. with $MnO_2$ in tetrahydrofuran, to the corresponding aldehyde of the formula X. This is reacted with an amine ($R^1$—O—Y—$NH_2$) with formation of a Schiffs base, which is immediately reduced to the corresponding secondary amine. The secondary amine can be alkylated to give the tertiary amine by known reactions, whereby the substituent $R^3$ is introduced into the molecule.

The amine can be prepared in various ways. In a preferred embodiment, it is identical with amines of the general formula XIII. m can assume values of between 1 and 3. The amine of the formula XIII is formed by alkylation of an alcohol $R^1$—OH with a nitrile of the formula XV with formation of a nitrile of the formula XIV and subsequent reduction to the corresponding primary amine.

A synthesis scheme for the compounds in which Z is not methylene includes the following steps:

Suzuki coupling (analogously to Example 2, see also A. Suzuki, N. Miyaura Chem. Rev. 1995, 95, 2457–2483; A. R. Martin, Y. Yang, Acta Chem. Scand. 1993, 47, 221–230);

Deprotonation with lithium diisopropylamide (LDA) and alkylation, fresh deprotonation and fresh alkylation (compare G. A. Molander et al. J. Org. Chem. 58, 1993, 7216–7227);

Hydrolysis using NaOH;

Curtius rearrangement (compare R. J. Sundberg, S. Jiang, Org. Prep. Proced. Int. 29, 1997, 117–122);

Alkylation with methyl bromoacetate (analogously to Example 2);

Reduction of the ester to the aldehyde with diisobutylaluminum hydride (DIBAH, compare J. Svoboda, J. Palecek, Collect. Czech. Chem. Commun. 56, 1991, 1317–1332);

Coupling of amine and aldehyde by reductive amination (analogously to Example 2).

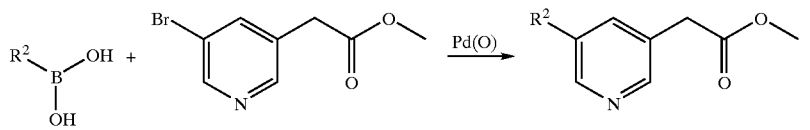

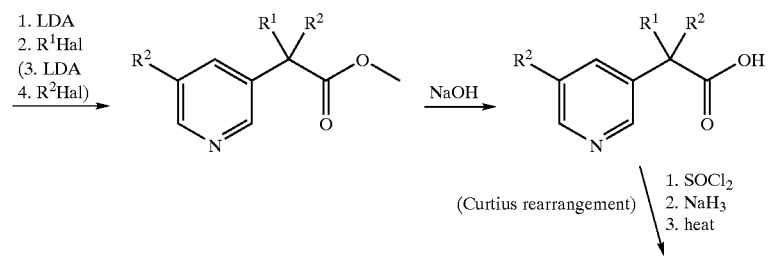

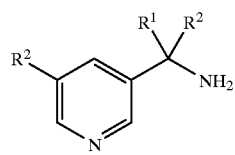

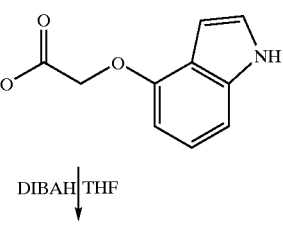

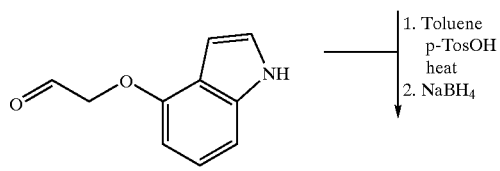

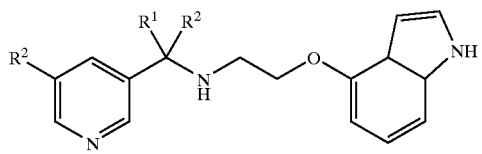

A further subject of the invention are compounds of the general formulae II, III, IV, V and VI, the substituents having the meanings already mentioned.

A further subject of the invention are compounds of the general formula IX, the substituents having the meanings already mentioned.

The invention is described by the following examples.

The molecular weight (M+H⁺) is determined with the aid of electron spray ionization mass spectroscopy. The mass-spectroscopic data derive from HPLC/MSC runs (HPLC coupled with an electrospray ionization mass spectrometer). The numerical values are, as customary in this procedure, not the molecular weights of the unmodified compounds, but the molecular weights of the protonated compounds (below: M+H⁺). The method is described in the following references:

M. Yamashita, J. B. Fenn, J. Phys. Chem. 88, 1984, 4451–4459; C. K. Meng et al., Zeitschrift für Physik D 10, 1988, 361–368; J. B. Fenn et al., Science 246, 1989, 64–71.

EXAMPLE 1

Preparation of the Compound 5-[(3-fluorophenyl)pyridin-3-ylmethyl]-[2-(2-methyl-1-H-indol-4-yloxy)ethyl]amine dihydrochloride.

The synthesis follows the synthesis scheme where the bromine atom of the formula VII is in the meta position relative to the pyridine nitrogen, $R^2$ is 3-fluorophenyl, Y is ethylene, X has the meaning of oxygen and $R^1$ is 2-methylindol-4-yl.

A solution of 113 g (607 mmol) of 5-bromopyridine-3-carbaldehyde, 41.9 ml (700 mmol) of ethanolamine and 12 g (10 mmol) of toluene-4-sulfonic acid monohydrate in 1 l of toluene is heated in a water separator for 5 hours. After cooling, 500 ml of methanol are added to the solution and 78.8 g (2.00 mol) of sodium borohydride are introduced in portions with stirring. The reaction mixture is stirred at room temperature for 18 hours, concentrated in vacuo and the residue is partitioned between water and ethyl acetate. The organic phase is evaporated: 2-[(5-bromopyridin-3-ylmethyl)amino]ethanol ((M+H⁺)=231.233) as a slightly yellowish oil which is employed for the next reaction without further purification.

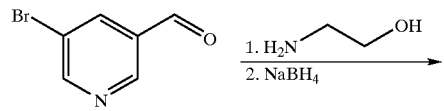

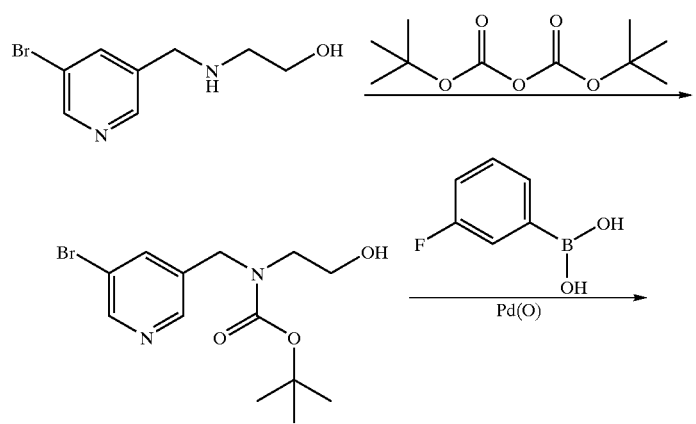

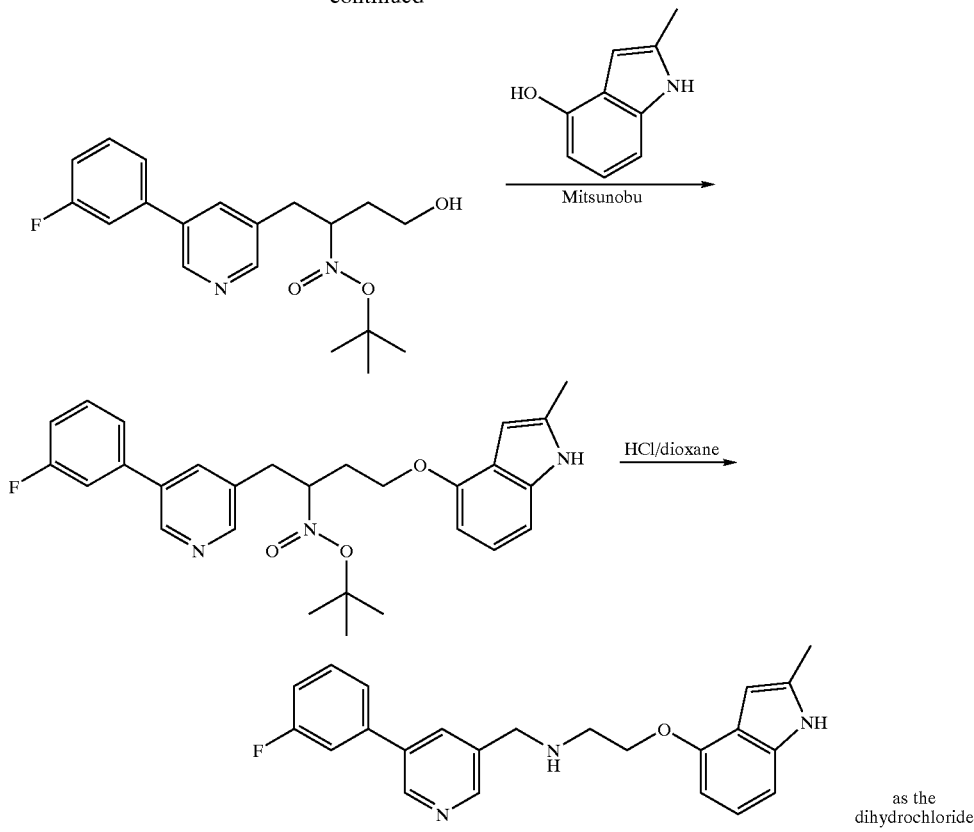

A solution of 164 g (750 mmol) of di-tert-butyl dicarbonate in 1 l of dichloromethane is slowly added dropwise to a solution of 120 g (about 519 mmol) of crude 2-[(5-bromopyridin-3-ylmethyl)amino]ethanol in 1 l of dichloromethane cooled to 0° C. The reaction mixture is stirred at room temperature for 18 hours, treated with 3 l of water and the organic phase is separated off. The organic phase is dried over sodium sulfate and concentrated, and the residue is chromatographed on a silica gel column using dichloromethane/methanol 9:1: tert-butyl (5-bromopyridin-3-ylmethyl)-(2-hydroxyethyl)carbamate ((M+H$^+$)=331.333) as a yellowish oil. A solution of 5.40 g (16.3 mmol) of tert-butyl (5-bromopyridin-3-ylmethyl)-(2-hydroxyethyl) carbamate, 4.6 g (32.9 mmol) of 3-fluorobenzeneboronic acid, 250 g (0.27 mmol) of tris(dibenzylideneacetone) dipalladium(0) and 220 mg (1.09 mmol) of tri-tert-butylphosphine in 200 ml of dioxane is treated with 10.6 g (32.5 mmol) of cesium carbonate and stirred at 100° C. for 4 hours. The reaction mixture is added to water and extracted with ethyl acetate. The organic phase is evaporated and the residue is chromatographed on a silica gel column using petroleum ether/ethyl acetate as eluent: tert-butyl [5-(3-fluorophenyl)pyridin-3-ylmethyl]-(2-hydroxyethyl) carbamate ((M+H$^+$)=347) as a colorless oil.

A solution of 100 mg (0.289 mmol) of tert-butyl [5-(3-fluorophenyl)pyridin-3-ylmethyl]-(2-hydroxyethyl) carbamate and 86.8 mg (0.590 mmol) of 4-hydroxy-2-methylindole in 5 ml of THF is treated with 240 mg of polymer-bound triphenylphosphine and stirred at room temperature for 10 minutes. 166 mg (720 mmol) of di-tert-butyl azodicarboxylate are then added and the mixture is stirred at room temperature for 18 hours. 1 g of strongly basic ion exchanger is then added, and the mixture is stirred for 1 hour and filtered. The filtrate is evaporated. The following compound is obtained: tert-butyl [5-(3-fluorophenyl)pyridin-3-ylmethyl]-[2-(2-methyl-1H-indol-4-yloxy)ethyl]carbamate ((M+H$^+$)=476) as a yellowish oil.

The crude tert-butyl [5-(3-fluorophenyl)pyridin-3-ylmethyl]-[2-(2-methyl-1H-indol-4-yloxy)ethyl]carbamate obtained in the previous example is treated with 2 ml of 4N hydrogen chloride in dioxane, diluted with 1 ml of methanol and stirred at room temperature for 2 hours. The reaction mixture is evaporated, and the residue is stirred with diethyl ether and filtered. The residue is partitioned between 1 N sodium hydroxide solution and ethyl acetate, the organic phase is evaporated and the residue is treated with an excess of 0.1 N HCl in isopropanol. The solvent is distilled off: 5-(3-fluorophenyl)pyridin-3-ylmethyl]-[2-(2-methyl-1H-indol-4-yloxy)ethyl]amine dihydrochloride as a brownish solid, (M+H$^+$)=376.

EXAMPLE 2

Preparation of the Compound 5-(4-fluorophenyl)pyridin-3-ylmethyl]-[2-(1H-indol-4-yloxy)ethyl]amine hydrochloride by an Alternative Synthesis Method.

A solution of 244 g (1.30 mol) of (5-bromopyridin-3-yl)methanol and 200 g (1.43 mol) of 4-fluorobenzeneboronic acid in 1.5 l of toluene is treated with 750 ml of water, 168 g (2.00 mol) of sodium hydrogencarbonate and 5.0 g (4.3 mmol) of tetrakis(triphenylphosphine)palladium(0) and heated to boiling for 24 hours. The organic phase is separated off, dried over sodium sulfate and evaporated. The residue is recrystallized from tert-butyl methyl ether: [5-(4-fluorophenyl)pyridin-3-yl]methanol as colorless crystals of m.p. 71–72° C.

A solution of 62.0 g (305 mmol) of [5-(4-fluorophenyl)pyridin-3-yl]methanol in 500 ml of THF is treated with 135 g (1.554 mol) of manganese dioxide and stirred at 45° C. for 18 hours. The reaction mixture is filtered and the filtrate is evaporated. The residue is recrystallized from tert-butyl methyl ether: 5-(4-fluorophenyl)pyridine-3-carbaldehyde as colorless crystals; (M+H$^+$) 202.

A solution of 1.00 g (7.51 mmol) of 4-hydroxyindole and 965 mg (7.80 mmol) of bromoacetonitrile in 30 ml of acetonitrile is treated with 2.6 g (8.0 mmol) of cesium carbonate and stirred at room temperature for 18 hours. The reaction mixture is filtered and the filtrate is evaporated: (1H-indol-4-yloxy)acetonitrile as a gray solid; (M+H$^+$): 173.

700 mg (3.972 mmol) of 2-(1H-indol-4-yloxy)ethylamine and 100 mg (0.52 mmol) of toluene-4-sulfonic acid monohydrate are added to a solution of 805 mg (4.00 mmol) of 5-(4-fluorophenyl)pyridine-3-carbaldehyde in 80 ml of toluene and the mixture is heated to boiling for 18 hours in a water separator. After cooling, the mixture is treated with 50 ml of methanol and 630 mg (16.0 mmol) of sodium borohydride are added. The reaction mixture is stirred at room temperature for 18 hours, concentrated in vacuo and the residue is partitioned between water and ethyl acetate. The organic phase is evaporated and the residue is chromatographed on a silica gel column using ethyl acetate/ethanol 8:2 as eluent: [5-(4-fluorophenyl)pyridin-3-ylmethyl]-[2-

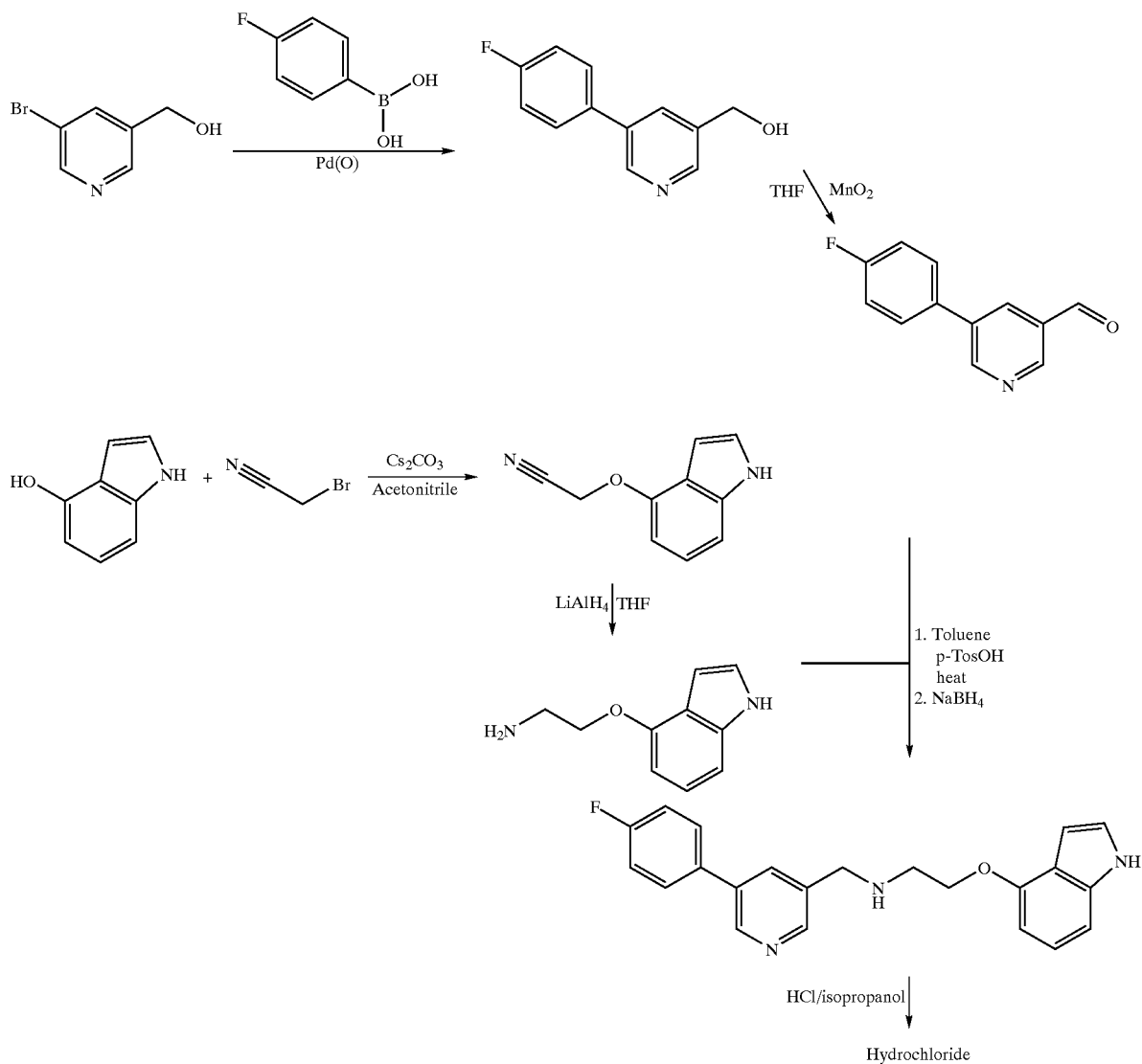

A solution of 1.20 g (6.97 mmol) of (1H-indol-4-yloxy)acetonitrile in 20 ml of THF cooled to 0° C. is treated with 531 mg (14.0 mmol) of lithium aluminum hydride and warmed to room temperature with stirring. After stirring at room temperature for 2 hours, the reaction mixture is treated with 2 g of sodium sulfate moistened with water and filtered. The filtrate is evaporated: 2-(1H-indol-4-yloxy)ethylamine as a yellowish oil; (M+H$^+$): 177.

(1H-indol-4-yloxy)-ethyl]amine as colorless crystals; (M+H$^+$) 362. The product thus obtained is treated with 3 ml of 0.1 N HCl in isopropanol and stirred at room temperature for one hour. The solvent is distilled off, and the residue is treated with diethyl ether and filtered: [5-(4-fluorophenyl)pyridin-3-ylmethyl]-[2-(1H-indol-4-yloxy)ethyl]amine hydrochloride as brownish crystals; (M+H$^+$) 362.

EXAMPLE 3

The following compounds are prepared analogously.

| No. | Structure | Name or salt form | (M + H⁺) |
|---|---|---|---|
| a | 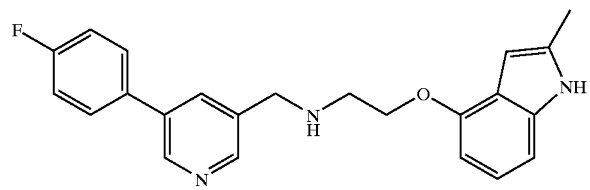 | [5-(4-fluorophenyl)-pyridin-3-ylmethyl]-[2-(2-methyl-1H-indol-4-yloxy)ethyl]amine hydrochloride | 376 |
| b | 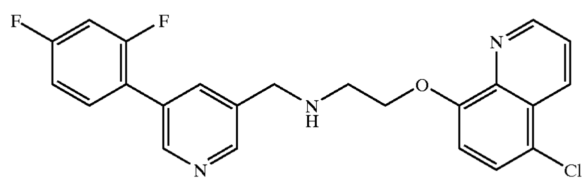 | [2-(5-chloroquinoline-8-yloxy)ethyl]-[5-(2,4-difluorophenyl)pyridin-3-ylmethyl]amine hydrochloride | 426 |
| c | 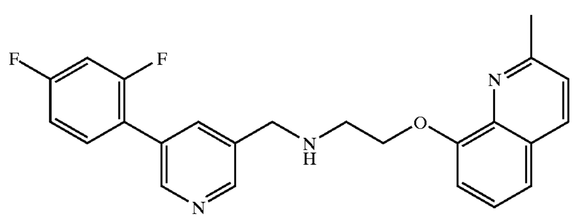 | [5-(2,4-difluorophenyl)-pyridin-3-ylmethyl]-[2-(2-methylquinolin-8-yloxy)ethyl]amine hydrochloride | 406 |
| d | 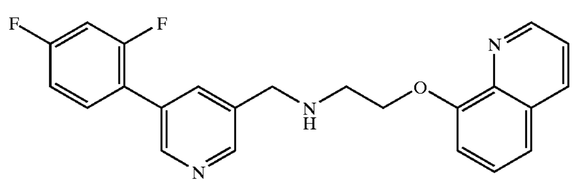 | [5-(2,4-difluorophenyl)-pyridin-3-ylmethyl]-[2-(quinolin-8-yloxy)ethyl]amine hydrochloride | 392 |
| e | 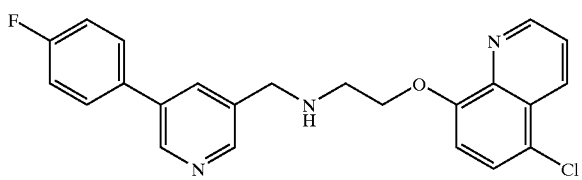 | [2-(5-chloroquinolin-8-yloxy)ethyl]-[5-(4-fluorophenyl)pyridin-3-ylmethyl]amine hydrochloride | 408 |
| f | 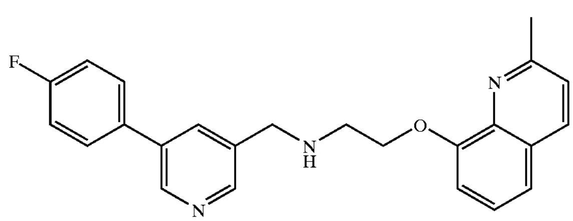 | [5-(4-fluorophenyl)-pyridin-3-ylmethyl]-[2-(2-methylquinolin-8-yloxy)ethyl]amine hydrochloride | 388 |
| g | 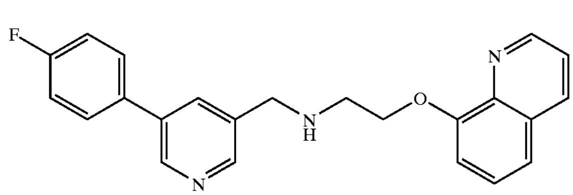 | [5-(4-fluorophenyl)-pyridin-3-ylmethyl]-[2-(quinolin-8-yloxy)-ethyl]amine hydrochloride | 374 |

| No. | Structure | Name or salt form | (M + H+) |
|---|---|---|---|
| h | 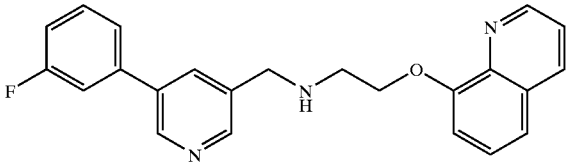 | [5-(3-fluorophenyl)-pyridin-3-ylmethyl]-[2-(quinolin-8-yloxy)-ethyl]amine hydrochloride | 374 |
| i | 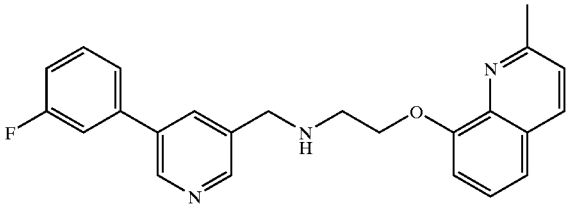 | [5-(3-fluorophenyl)-pyridin-3-ylmethyl]-[2-(2-methylquinolin-8-yloxy)ethyl]amine hydrochloride | 388 |
| j | 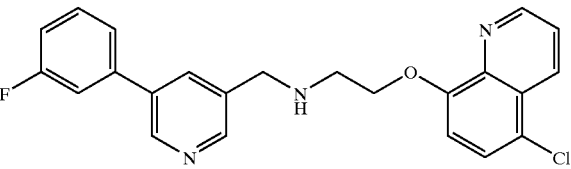 | [2-(5-chloroquinolin-8-yloxy)ethyl]-[5-(3-fluorophenyl)pyridin-3-ylmethyl]amine hydrochloride | 408 |
| k | 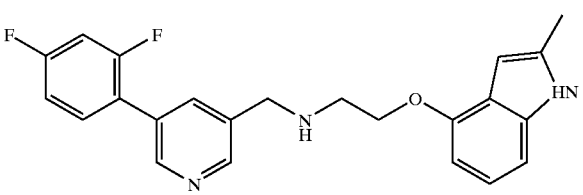 | [5-(2,4-difluorophenyl)-pyridin-3-ylmethyl]-[2-(2-methyl-1H-indol-4-yloxy)ethyl]amine hydrochloride | 394 |
| l | 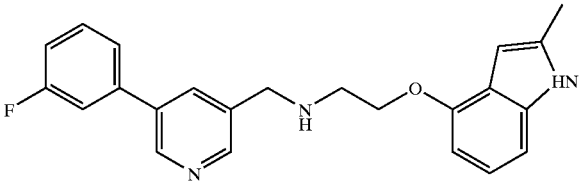 | [5-(3-fluorophenyl)-pyridin-3-ylmethyl]-[2-(2-methyl-1H-indol-4-yloxy)ethyl]amine hydrochloride | 376 |
| m | 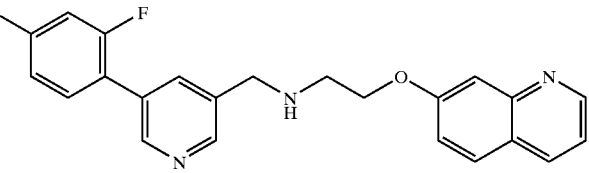 | [5-(2,4-difluorophenyl)-pyridin-3-ylmethyl]-[2-(quinolin-7-yloxy)-ethyl]amine hydrochloride | 392 |
| n | 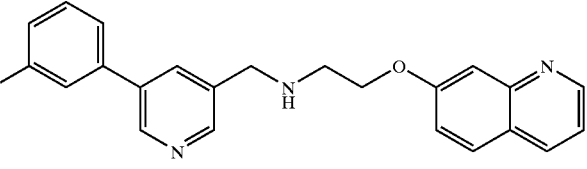 | [5-(3-fluorophenyl)-pyridin-3-ylmethyl]-[2-(quinolin-7-yloxy)-ethyl]amine hydrochloride | 374 |
| o | 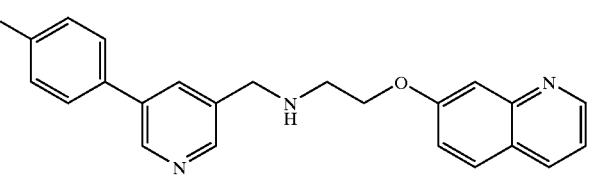 | [5-(4-fluorophenyl)-pyridin-3-ylmethyl]-[2-(quinolin-7-yloxy)-ethyl]amine hydrochloride | 374 |

-continued

| No. | Structure | Name or salt form | (M + H⁺) |
|---|---|---|---|
| p | 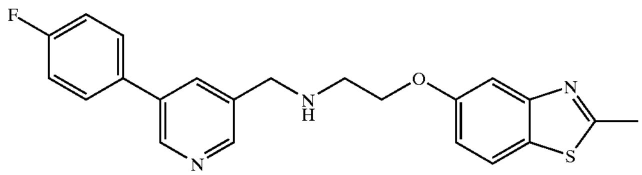 | [5-(4-fluorophenyl)-pyridin-3-ylmethyl]-[2-(2-methylbenzothiazol-5-yloxy)ethyl]amine dihydrochloride | 394 |
| q | 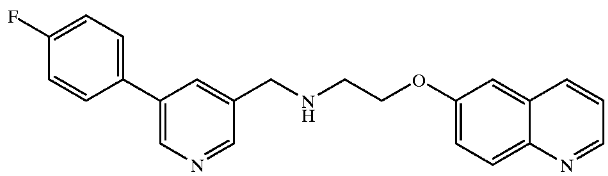 | [5-(4-fluorophenyl)-pyridin-3-ylmethyl]-[2-(quinolin-6-yloxy)-ethyl]amine trihydrochloride | 374 |
| r | 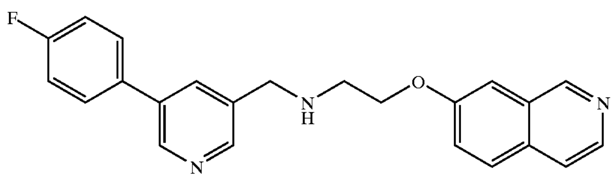 | [5-(4-fluorophenyl)-pyridin-3-ylmethyl]-[2-(isoquinolin-7-yloxy)-ethyl]amine trihydrochloride | 374 |
| s | 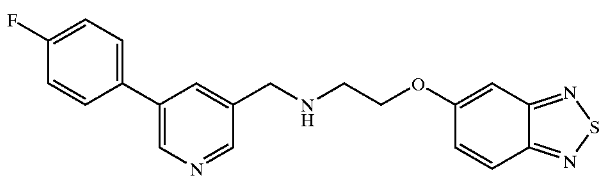 | [2-(benzo[1,2,5]thiadiazol-5-yloxy)ethyl]-[5-(4-fluorophenyl)-pyridin-3-ylmethyl]-amine dihydrochloride | 381 |
| t | 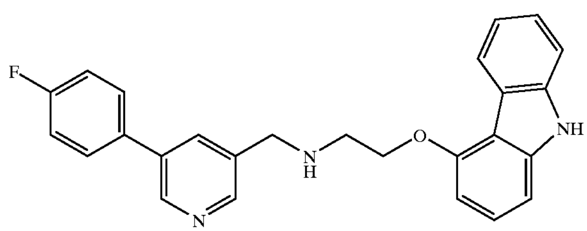 | [2-(9H-carbazol-4-yloxy)ethyl]-[5-(4-fluorophenyl)pyridin-3-ylmethyl]amine dihydrochloride | 412 |
| u | 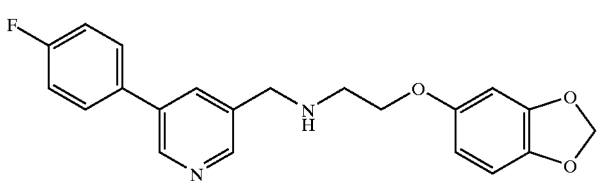 | [2-(benzo[1,3]dioxol-5-yloxy)ethyl]-[5-(4-fluorophenyl)pyridin-3-ylmethyl]amine dihydrochloride | 367 |
| v | 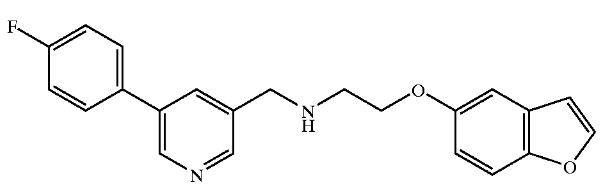 | [2-(benzofuran-5-yloxy)ethyl][5-(4-fluorophenyl)pyridin-3-ylmethyl]amine dihydrochloride | 363 |
| w | 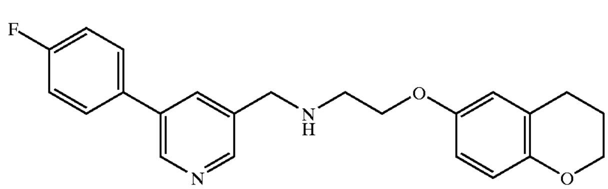 | [2-(chroman-6-yloxy)-ethyl]-[5-(4-fluorophenyl)pyridin-3-ylmethyl]amine dihydrochloride | 448 |

| No. | Structure | Name or salt form | (M + H⁺) |
|---|---|---|---|
| x | 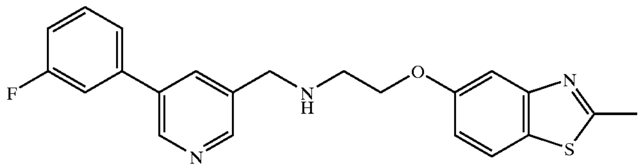 | [5-(3-fluorophenyl)-pyridin-3-ylmethyl]-[2-(2-methylbenzothiazol-5-yloxy)ethyl]amine dihydrochloride | 394 |
| y | 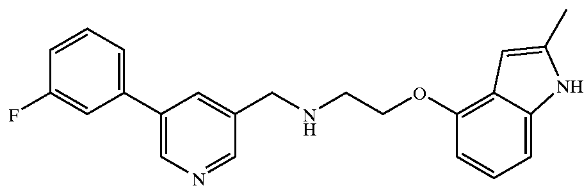 | [5-(3-fluorophenyl)-pyridin-3-ylmethyl]-[2-(2-methyl-1H-indol-4-yloxy)ethyl]amine dihydrochloride | 376 |
| z | 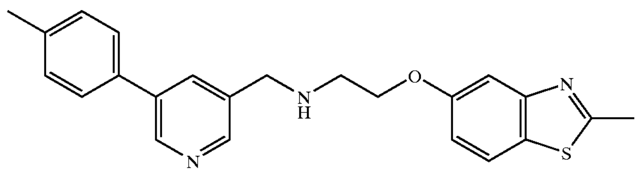 | [2-(2-methyl-benzothiazol-5-yloxy)-ethyl]-(5-p-tolylpyridin-3-ylmethyl)amine dihydrochloride | 390 |
| aa | 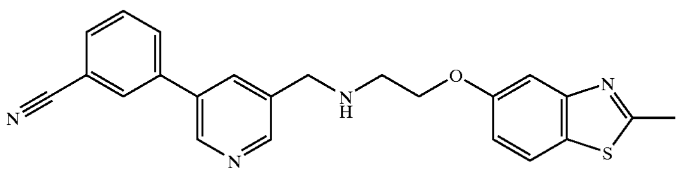 | 3-(5-{[2-(2-methyl benzothiazol-5-yloxy)-ethylamino]methyl}-pyridin-3-yl)benzonitrile dihydrochloride | 401 |
| bb | 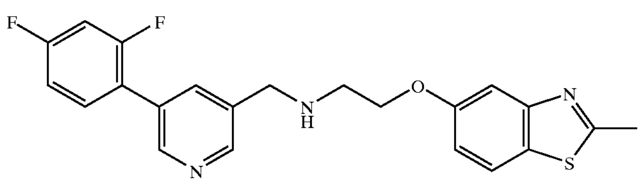 | [5-(2,4-difluorophenyl)-pyridin-3-ylmethyl]-[2-(2-methylbenzothiazol-5-yloxy)ethyl]amine dihydrochloride | 412 |
| cc | 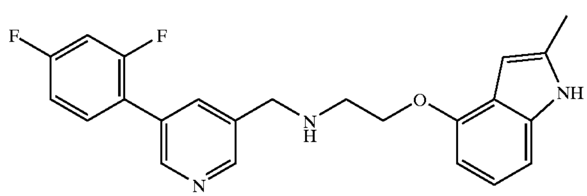 | [5-(2,4-difluorophenyl)-pyridin-3-ylmethyl]-[2-(2-methyl-1H-indol-4-yloxy)ethyl]amine dihydrochloride | 394 |
| dd | 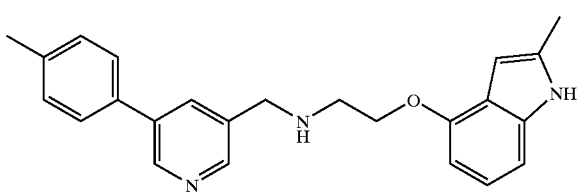 | [2-(2-methyl-1H-indol-4-yloxy)ethyl]-(5-p-tolylpyridin-3-ylmethyl)amine dihydrochloride | 372 |
| ee | 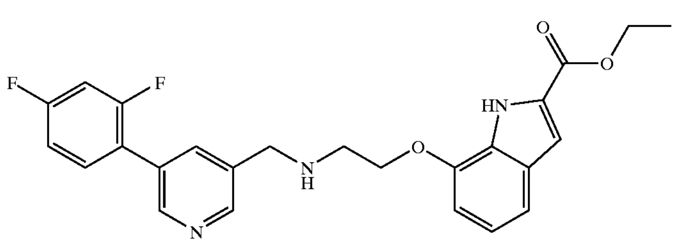 | ethyl 7-(2-{[5-(2,4-difluorophenyl)pyridin-3-ylmethyl]amino}-ethoxy)-1H-indol-2-carboxylate dihydrochloride | 452 |

-continued

| No. | Structure | Name or salt form | (M + H+) |
|---|---|---|---|
| ff | 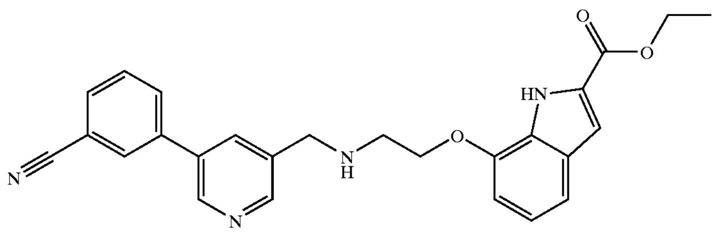 | ethyl 7-(2-{[5-(3-cyanophenyl)pyridin-3-ylmethyl]amino}-ethoxy)-1H-indol-2-carboxylate dihydrochloride | 441 |
| gg | 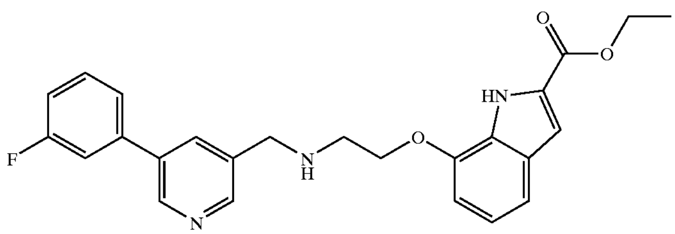 | ethyl 7-(2-{[5-(3-fluorophenyl)pyridin-3-ylmethyl]amino}-ethoxy)-1H-indol-2-carboxylate dihydrochloride | 434 |
| hh | 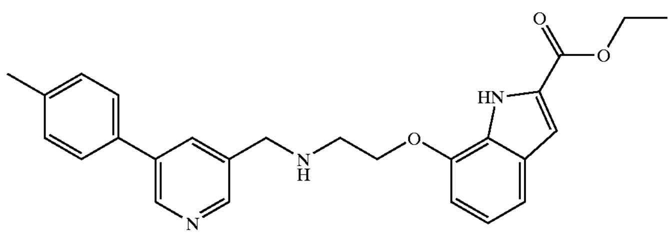 | ethyl 7-{2-[(5-p-tolyl-pyridin-3-ylmethyl)-amino]ethoxy}-1H-indole-2-carboxylate dihydrochloride | 413 |
| ii | 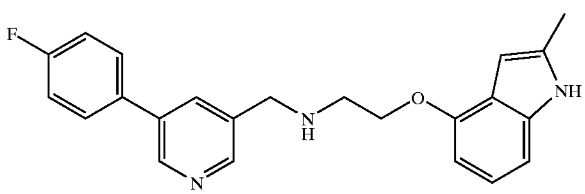 | [5-(4-fluorophenyl)-pyridin-3-ylmethyl]-[2-(2-methyl-1H-indol-4-yloxy)ethyl]amine dihydrochloride | 376 |
| jj | 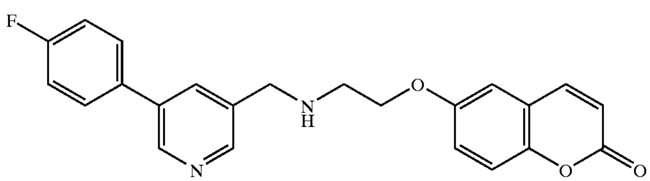 | 6-(2-{[5-(4-fluorophenyl)pyridin-3-ylmethyl]amino}-ethoxy)chromen-2-one dihydrochloride | 391 |
| kk | 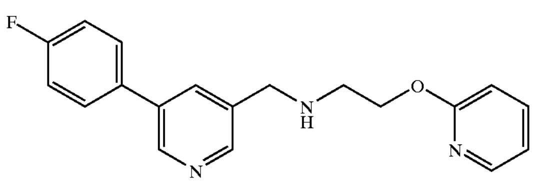 | [5-(4-fluorophenyl)-pyridin-3-ylmethyl]-[2-(pyridin-2-yloxy)ethyl]-amine trihydrochloride | 324 |
| ll | 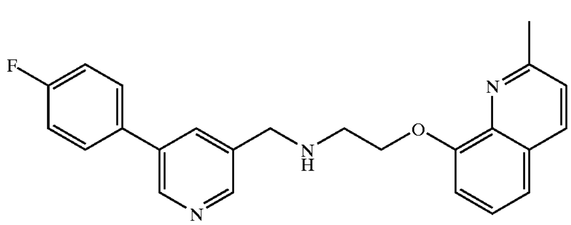 | [5-(4-fluorophenyl)-pyridin-3-ylmethyl]-[2-(2-methylquinolin-8-yloxy)ethyl]amine trihydrochloride | 388 |

| No. | Structure | Name or salt form | (M + H⁺) |
|---|---|---|---|
| mm | 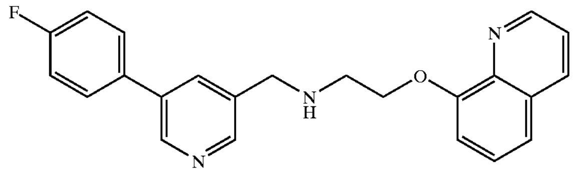 | [5-(4-fluorophenyl)-pyridin-3-ylmethyl]-[2-(quinolin-8-yloxy)-ethyl]amine trihydrochloride | 374 |
| nn | 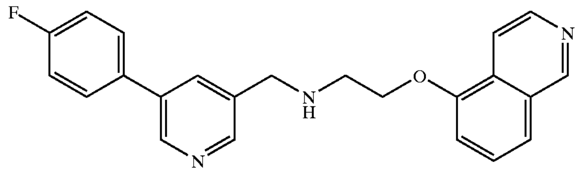 | [5-(4-fluorophenyl)-pyridin-3-ylmethyl]-[2-(isoquinolin-5-yloxy)-ethyl]amine trihydrochloride | 374 |
| oo | 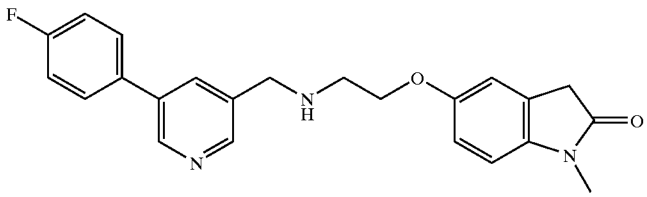 | 5-(2-{[5-(4-fluorophenyl)pyridin-3-ylmethyl]amino}-ethoxy)-1-methyl-1,3-dihydroindol-2-one dihydrochloride | 392 |
| pp | 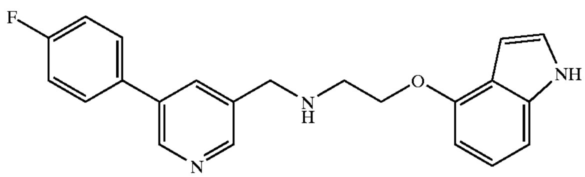 | [5-(4-fluorophenyl)-pyridin-3-ylmethyl]-[2-(1H-indol-4-yloxy)-ethyl]amine hydrochloride | 362 |
| qq | 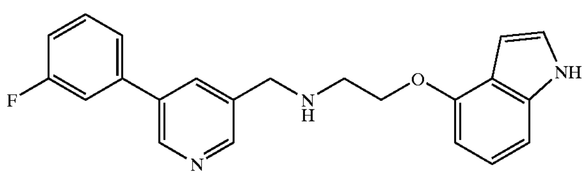 | [5-(3-fluorophenyl)-pyridin-3-ylmethyl]-[2-(1H-indol-4-yloxy)-ethyl]amine hydrochloride | 362 |
| rr | 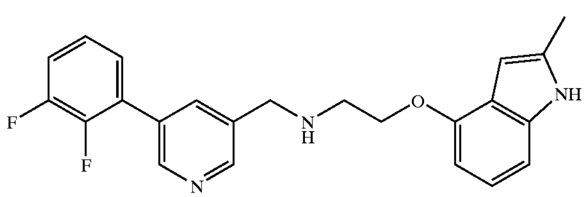 | [5-(2,3-difluorophenyl)-pyridin-3-ylmethyl]-[2-(2-methyl-1H-indol-4-yloxy)ethyl]amine hydrochloride | 394 |
| ss | 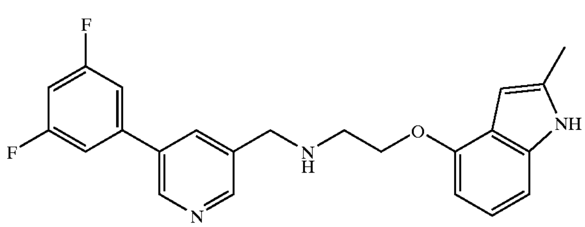 | [5-(3,5-difluorophenyl)-pyridin-3-ylmethyl]-[2-(2-methyl-1H-indol-4-yloxy)ethyl]amine hydrochloride | 394 |
| tt | 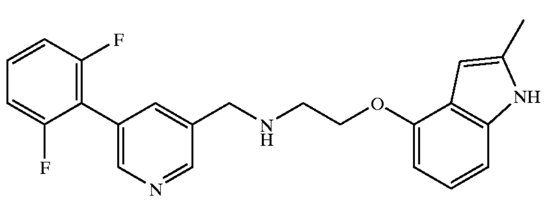 | [5-(2,6-difluorophenyl)-pyridin-3-ylmethyl]-[2-(2-methyl-1H-indol-4-yloxy)ethyl]amine hydrochloride | 394 |

-continued

| No. | Structure | Name or salt form | (M + H⁺) |
|---|---|---|---|
| uu | 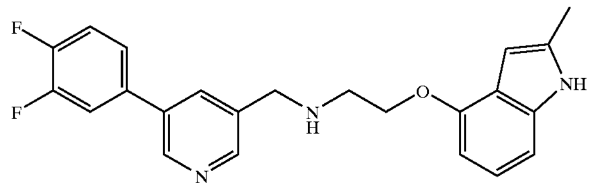 | [5-(3,4-difluorophenyl)-pyridin-3-ylmethyl]-[2-(2-methyl-1H-indol-4-yloxy)ethyl]amine hydrochloride | 394 |
| vv | 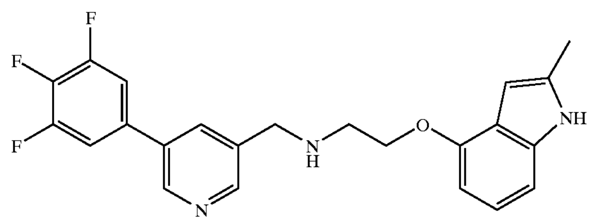 | [2-(2-methyl-1H-indol-4-yloxy)ethyl]-[5-(3,4,5-trifluorophenyl)-pyridin-3-ylmethyl]-amine hydrochloride | 412 |
| ww | 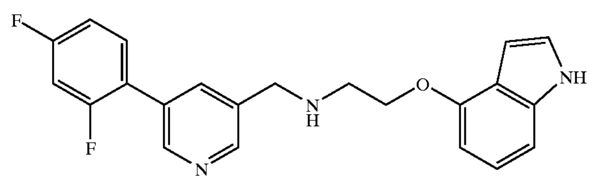 | [5-(2,4-difluoro-phenyl)pyridin-3-ylmethyl]-[2-(1H-indol-4-yloxy)ethyl]amine hydrochloride | 380 |
| xx | 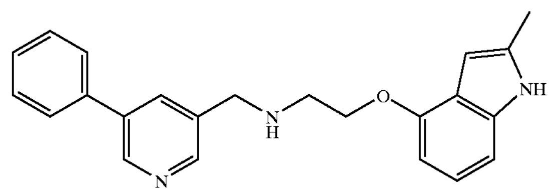 | [2-(2-methyl-1H-indol-4-yloxy)ethyl]-(5-phenylpyridin-3-ylmethyl)amine hydrochloride | 358 |
| yy | 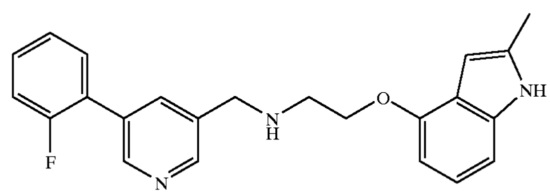 | [5-(2-fluorophenyl)-pyridin-3-ylmethyl]-[2-(2-methyl-1H-indol-4-yloxy)ethyl]amine hydrochloride | 376 |
| zz | 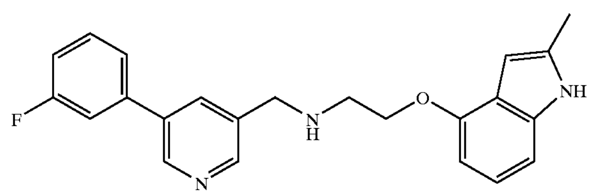 | [5-(3-fluorophenyl)-pyridin-3-ylmethyl]-[2-(2-methyl-1H-indol-4-yloxy)-ethyl]-amine methanesulfonate | 376 |
| aaa | 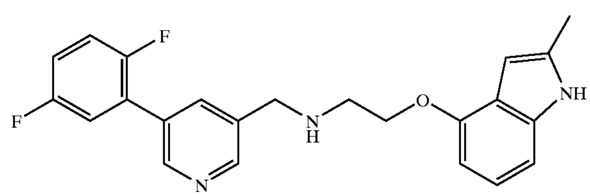 | [5-(2,5-difluorophenyl)-pyridin-3-ylmethyl]-[2-(2-methyl-1H-indol-4-yloxy)-ethyl]-amine hydrochloride | 394 |
| bbb | 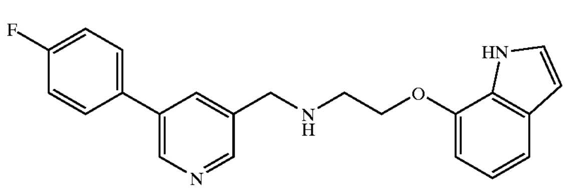 | [5-(4-fluorophenyl)-pyridin-3-ylmethyl]-[2-(1H-indol-7-yloxy)-ethyl]-amine hydrochloride | 362 |

-continued

| No. | Structure | Name or salt form | (M + H⁺) |
|---|---|---|---|
| ccc | 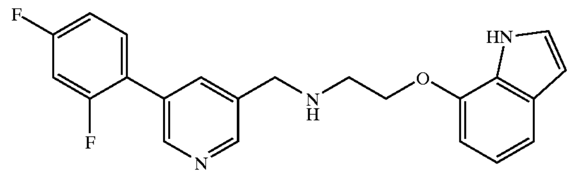 | [5-(2,4-difluorophenyl)-pyridin-3-ylmethyl]-[2-(1H-indol-7-yloxy)-ethyl]-amine hydrochloride | 380 |
| ddd | 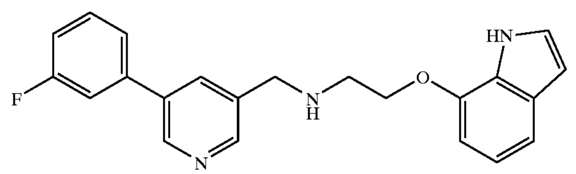 | [5-(3-fluorophenyl)-pyridin-3-ylmethyl]-[2-(1H-indol-7-yloxy)-ethyl]amine hydrochloride | 362 |
| eee | 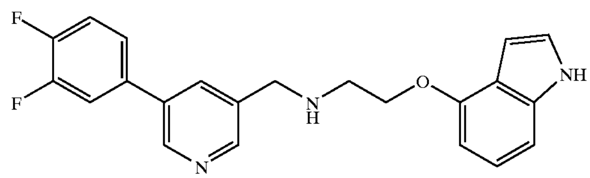 | [5-(3,4-difluorophenyl)-pyridin-3-ylmethyl]-[2-(1H-indol-4-yloxy)-ethyl]-amine hydrochloride | 380 |
| fff | 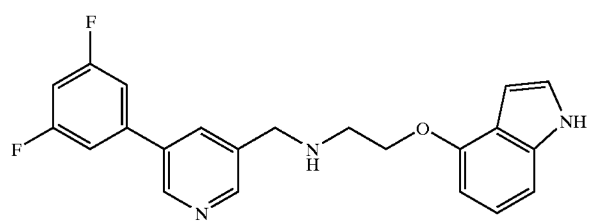 | [5-(3,5-difluorophenyl)-pyridin-3-ylmethyl]-[2-(1H-indol-4-yloxy)-ethyl]-amine hydrochloride | 380 |
| ggg | 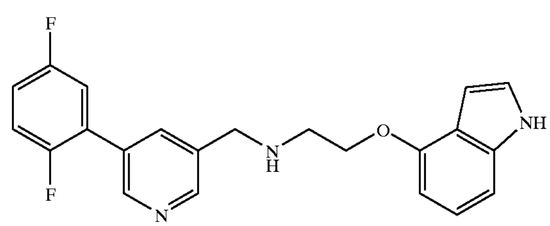 | [5-(2,5-difluorophenyl)-pyridin-3-ylmethyl]-[2-(1H-indol-4-yloxy)-ethyl]-amine hydrochloride | 380 |
| hhh | 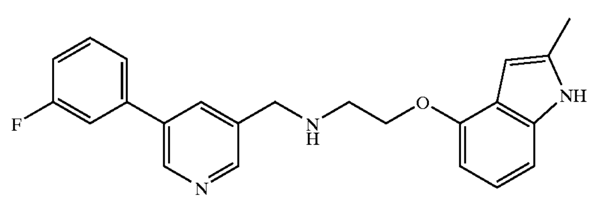 | [5-(3-fluorophenyl)-pyridin-3-ylmethyl]-[2-(2-methyl-1H-indol-4-yloxy)-ethyl]-amine malonate | 376 |
| iii | 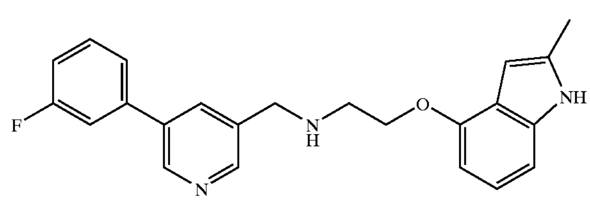 | [5-(3-fluorophenyl)-pyridin-3-ylmethyl]-[2-(2-methyl-1H-indol-4-yloxy)-ethyl]-amine hemifumarate | 376 |

-continued

| No. | Structure | Name or salt form | (M + H⁺) |
|---|---|---|---|
| jjj | 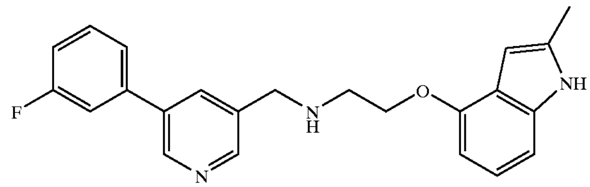 | [5-(3-fluorophenyl)-pyridin-3-ylmethyl]-[2-(2-methyl-1H-indol-4-yloxy)-ethyl]-amine hemisulfate | 376 |
| kkk | 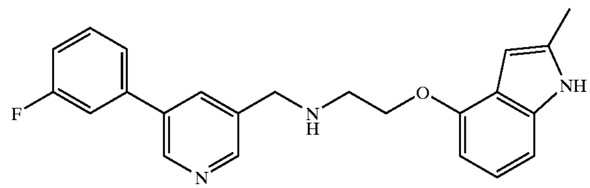 | [5-(3-fluorophenyl)-pyridin-3-ylmethyl]-[2-(2-methyl-1H-indol-4-yloxy)-ethyl]-amine tartrate | 376 |
| lll | 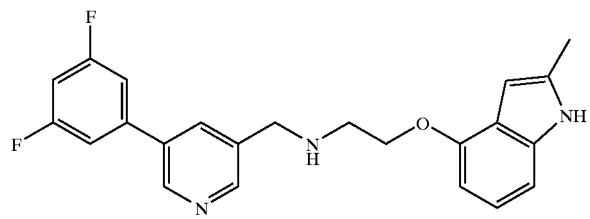 | [5-(3,5-difluorophenyl)-pyridin-3-ylmethyl]-[2-(2-methyl-1H-indol-4-yloxy)-ethyl]-amine hemifumarate | 394 |
| mmm | 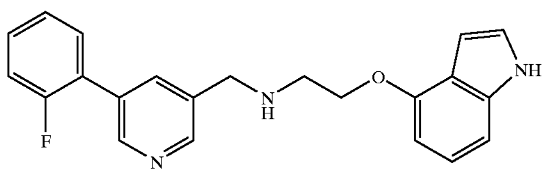 | [5-(2-fluorophenyl)-pyridin-3-ylmethyl]-[2-(1H-indol-4-yloxy)-ethyl]-amine dihydrochloride | 362 |
| nnn | 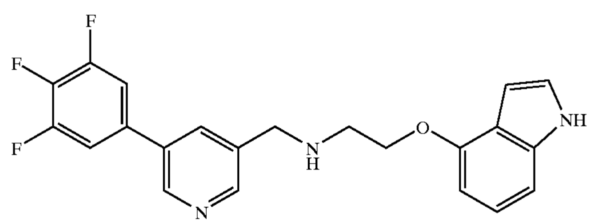 | [2-(1H-indol-4-yloxy)-ethyl]-[5-(3,4,5-trifluorophenyl)-pyridin-3-ylmethyl]-amine dihydrochloride | 398 |
| ooo | 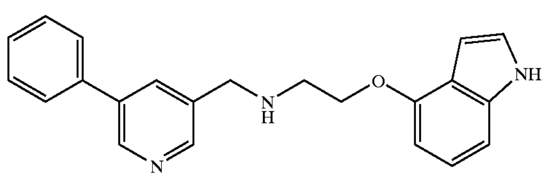 | [2-(1H-indol-4-yloxy)-ethyl]-(5-phenyl-pyridin-3-ylmethyl)-amine dihydrochloride | 344 |

EXAMPLE 4

Ampoules for Injection

A solution of 100 g of a compound of the general formula I and 5 g of disodium hydrogenphosphate is adjusted to pH 6.5 using 2 N hydrochloric acid in 3 l of double-distilled water, sterile filtered and filled into injection ampoules, and lyophilized. Sterile conditions were adhered to here. Each injection ampoule contains 5 mg of the active component of the general formula I.

EXAMPLE 5

A mixture of 20 g of a compound of the general formula I is mixed with 100 g of soya lecithin and 1400 g of cocoa butter with warming and poured into hollows. Each suppository contains 20 mg of the active component.

EXAMPLE 6

A solution comprising 1 g of a compound of the general formula I, 9.38 g of $NaH_2PO_4 \times 2\ H_2O$, 28.48 g of $Na_2HPO_4 \times 12\ H_2O$ and 0.1 g of benzalkonium chloride is prepared using 940 ml of double-distilled water. The solution is adjusted to pH 6.8 and made up to one liter with double-distilled water and sterilized by irradiation. This solution can be used in the form of eye drops.

EXAMPLE 7

Ointment 500 mg of a compound of the general formula I are blended with 99.5 g of raw petroleum jelly under aseptic conditions.

EXAMPLE 8

Tablets 100 g of a compound of the general formula I, 1 kg of lactose, 600 g of microcrystalline cellulose, 600 g of cornstarch, 100 g of polyvinyl-pyrrolidone, 80 g of talc and 10 g of magnesium stearate are mixed and pressed in a customary manner to give tablets such that one tablet contains 100 mg of the active component.

EXAMPLE 9

Coated Tablets

Tablets are prepared as in Example 7 and then coated in a known manner with sucrose, maize starch, talc, tragacanth gum and colorants.

EXAMPLE 10

Capsules

Hard gelatin capsules are filled with a compound of the general formula I in a known manner such that each capsule contains 5 mg of the active component.

EXAMPLE 11

Inhalation Spray 14 g of a compound of the general formula I are dissolved in 10 l of isotonic saline solution. The solution is filled into commercially obtainable spray containers which have a pump mechanism. The solution can be sprayed into the mouth or into the nose. One puff of spray (approximately 0.1 ml) corresponds to a dose of 0.14 mg of a compound of the general formula I.

What is claimed is:

1. A compound of the formula I

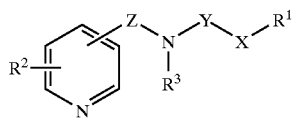

(I)

where $R^1$ is a heterocycle radical which is quinolyl or isoquinolyl optionally substituted by at least one chlorine, or indolyl, benzothiazolyl, coumaronyl, coumarinyl, pyridyl, or carbazolyl, wherein quinolyl, isoquinolyl, indolyl, or benzothiazolyl is optionally substituted with a methyl group or an ethoxycarbonyl group and the heterocycle radical is optionally monosubstituted, disubstituted or trisubstituted by one or more of the groups -A, —$OR^4$, —$N(R^4)_2$, —$NO_2$, —CN, Hal, —$COOR^4$, —$CON(R^4)_2$, —$COR^4$, or =O;

$R^2$ is a phenyl group which is optionally monosubstituted, disubstituted, trisubstituted, tetrasubstituted or pentasubstituted by one or more of the groups Hal, -A, —O-A, —$NO_2$ or —CN, or is a thienyl group which is optionally monosubstituted or disubstituted by one or more of the groups Hal, -A, —O-A, —$NO_2$, —CN or thienyl;

$R^3$ is H, -A, —CO-A, —$C(R^4)_2R^2$, or —$C(R^4)_2$-pyridinediyl-$R^2$;

$R^4$ is H or —A;

A is $C_1$-$C_6$-alkyl, where 1 to 7 hydrogen atoms are optionally replaced by fluorine;

—X— is —O—, —S—, sulfinyl, sulfonyl, or —$C(R^4)_2$—;

—Y— is —$[C(R^4)_2]_n$—;

—Z— is —$C(R^4)_2$—;

Hal is F, Cl, Br or I; and n is 1, 2, 3 or 4;

or a salt or solvate thereof.

2. A compound according to claim 1, wherein Z is in the meta position relative to the nitrogen of the pyridine ring connected to Z.

3. A compound according to claim 1, wherein:

Z is methylene,

Y is ethylene, $R^3$ is H, and/or

X is oxygen.

4. A compound according to claim 1, wherein $R^2$ is in the meta position relative to the nitrogen of the pyridine ring connected to $R^2$.

5. A compound according to claim 1, wherein:

$R^1$ is quinolyl, isoquinolyl, which optionally has at least one chlorine substituent, or indolyl, benzothiazolyl, coumaronyl, coumarinyl, pyridyl or carbazolyl, where optionally at least one hydrogen of the quinolyl, isoquinolyl, indolyl or benzothiazolyl is replaced by a methyl group or ethoxycarbonyl group; and/or $R^2$ is fluorophenyl, difluorophenyl, cyanophenyl or tolyl.

6. A compound according to claim 1, wherein:

$R^1$ is quinolin-7-yl, quinolin-8-yl, where a hydrogen is optionally replaced by a chlorine atom in position 5, or indol-4-yl or indol-7-yl, where a hydrogen in position 2 of the quinolyl or indolyl is optionally replaced by a methyl group or ethoxycarbonyl group; and/or $R^2$ is fluorophenyl, 2,4-difluorophenyl, 3-cyanophenyl or 4-methylphenyl.

7. A compound according to claim 1, of:

a) [5-(4-fluorophenyl)pyridin-3-ylmethyl]-[2-(2-methyl-1H-indol-4-yloxy)-ethyl]amine hydrochloride b) [2-(5-chloroquinolin-8-yloxy)ethyl]-[5-(2,4-difluorophenyl)pyridin-3-ylmethyl]amine hydrochloride c) [5-(2,4-difluorophenyl)pyridin-3-ylmethyl]-[2-(2-methylquinolin-8-yloxy)ethyl]amine hydrochloride d) [5-(2,4-difluorophenyl)pyridin-3-ylmethyl]-[2-(quinolin-8-yloxy)ethyl]-amine hydrochloride e) [2-(5-chloroquinolin-8-yloxy)ethyl]-[5-(4-fluorophenyl)pyridin-3-ylmethyl]amine hydrochloride f) [5-(4-fluorophenyl)pyridin-3-ylmethyl]-[2-(2-methylquinolin-8-yloxy)-ethyl]amine hydrochloride g) [5-(4-fluorophenyl)pyridin-3-ylmethyl]-[2-(quinolin-8-yloxy)ethyl]-amine hydrochloride h) [5-(3-fluorophenyl)pyridin-3-ylmethyl]-[2-(quinolin-8-yloxy)ethyl]-amine hydrochloride i) [5-(3-fluorophenyl)pyridin-3-ylmethyl]-[2-(2-methylquinolin-8-yloxy)-ethyl]amine hydrochloride j) [2-(5-chloroquinolin-8-yloxy)ethyl]-[5-(3-fluorophenyl)pyridin-3-ylmethyl]amine hydrochloride k) [5-(2,4-difluorophenyl)pyridin-3-ylmethyl]-[2-(2-methyl-1H-indol-4-yloxy)ethyl]amine hydrochloride l) [5-(3-fluorophenyl)pyridin-3-ylmethyl]-[2-(2-methyl-1H-indol-4-yloxy)-ethyl]amine hydrochloride m) [5-(2,4-difluorophenyl)pyridin-3-ylmethyl]-[2-(quinolin-7-yloxy)ethyl]-amine hydrochloride n) [5-(3-fluorophenyl)pyridin-3-ylmethyl]-[2-(quinolin-7-yloxy)ethyl]-amine hydrochloride o) [5-(4-fluorophenyl)pyridin-3-ylmethyl]-[2-(quinolin-7-yloxy)ethyl]-amine hydrochloride p) [5-(4-fluorophenyl)pyridin-3-ylmethyl]-[2-(2-methylbenzothiazol-5-yloxy)ethyl]-amine dihydrochloride q) [5-(4-fluorophenyl)pyridin-3-ylmethyl]-[2-(quinolin-6-yloxy)ethyl]-amine trihydrochloride r) [5-(4-fluorophenyl)pyridin-3-ylmethyl]-[2-(isoquinolin-7-yloxy)ethyl]-amine trihydrochloride s) [2-(benzo[1,2,5]thiadiazol-5-yloxy)ethyl]-[5-(4-fluorophenyl)pyridin-3-ylmethyl]amine dihydrochloride t) [2-(9H-carbazol-4-yloxy)ethyl]-[5-(4fluorophenyl)pyridin-3-ylmethyl]-amine dihydrochloride u) [2-(benzo[1,3]dioxol-5-yloxy)ethyl]-[5-(4-fluorophenyl)pyridin-3-ylmethyl]-amine dihydrochloride v) [2-(benzofuran-5-yloxy)ethyl]-[5 -(4-fluorophenyl)pyridin-3-ylmethyl]-amine dihydrochloride w) [2-(chroman-6-yloxy)ethyl]-[5-(4-fluorophenyl)pyridin-3-ylmethyl]-amine dihydrochloride x) [5-(3-fluorophenyl)pyridin-3-ylmethyl]-[2-(2-methylbenzothiazol-5-yloxy)ethyl]amine dihydrochloride y) [5-(3-fluorophenyl)pyridin-3-ylmethyl]-[2-(2-methyl-1H-indol-4-yloxy)-ethyl]amine dihydrochloride z) [2-(2-methylbenzothiazol-5-yloxy)ethyl]-(5-p-tolylpyridin-3-ylmethyl)-amine dihydrochloride aa) 3-(5-{[2-(2-methylbenzothiazol-5-yloxy)ethylamino]methyl}pyridin-3-yl)benzonitrile dihydrochloride bb) [5-(2,4-difluorophenyl)pyridin-3-ylmethyl]-[2-(2-methylbenzothiazol-5-yloxy)ethyl]amine dihydrochloride cc) [5-(2,4-difluorophenyl)pyridin-3-ylmethyl]-[2-(2-methyl-1H-indol-4-yloxy)ethyl]amine dihydrochloride dd) [2-(2-methyl-1H-indol-4-yloxy)ethyl]-(5-p-tolylpyridin-3-ylmethyl)-amine dihydrochloride ee) ethyl 7-(2-{[5-(2,4-difluorophenyl)pyridin-3-ylmethyl]amino}ethoxy)-1H-indole-2-carboxylate dihydrochloride ff) ethyl 7-(2-{[5-(3-cyanophenyl)pyridin-3-ylmethyl]amino}ethoxy)-1H-indole-2-carboxylate dihydrochloride gg) ethyl 7-(2-{[5-(3-fluorophenyl)pyridin-3-ylmethyl]amino}ethoxy)-1H-indole-2-carboxylate dihydrochloride hh) ethyl 7-{2-[(5-p-tolylpyridin-3-ylmethyl)amino]ethoxy}-1H-indole-2-carboxylate dihydrochloride ii) [5-(4-fluorophenyl)pyridin-3-ylmethyl]-[2-(2methyl-1H-indol-4-yloxy)-ethyl]amine dihydrochloride kk) [5-(4-fluorophenyl)pyridin-3-ylmethyl]-[2-(pyridin-2-yloxy)ethyl]-amine trihydrochloride ll) [5-(4-fluorophenyl)pyridin-3-ylmethyl]-[2-(methylquinolin-8-yloxy)-ethyl]amine trihydrochloride mm) [5-(4-fluorophenyl)pyridin-3-ylmethyl]-[2-(quinolin-8-yloxy)ethyl]-amine trihydrochloride nn) [5-(4-fluorophenyl)pyridin-3-ylmethyl]-[2-(isoquinolin-5-yloxy)ethyl]-amine trihydrochloride oo) 5-(2-{[5-(4-fluorophenyl)pyridin-3-ylmethyl]amino}ethoxy)-1-methyl-1,3-dihydroindol-2-one dihydrochloride pp) [5-(4-fluorophenyl)pyridin-3-ylmethyl]-[2-(1H-indol-4-yloxy)ethyl]-amine hydrochloride qq) [5-(3-fluorophenyl)pyridin-3-ylmethyl]-[2-(1H-indol-4-yloxy)ethyl]-amine hydrochloride rr) [5-(2,3-difluorophenyl)pyridin-3-ylmethyl]-[2-(2-methyl-1H-indol-4-yloxy)ethyl]amine hydrochloride ss) [5-(3,5-difluorophenyl)pyridin-3-ylmethyl]-[2-(2-methyl-1H-indol-4-yloxy)ethyl]amine hydrochloride tt) [5-(2,6-difluorophenyl)pyridin-3-ylmethyl]-[2-(2-methyl-1H-indol-4-yloxy)ethyl]amine hydrochloride uu) [5-(3,4-difluorophenyl)pyridin-3-ylmethyl]-[2-(2methyl-1H-indol-4-yloxy)ethyl]amine hydrochloride vv) [2-(2-methyl-1H-indol-4-yloxy)ethyl]-[5-(3,4,5-trifluorophenyl)pyridin-3-ylmethyl]amine hydrochloride ww) [5-(2,4-difluorophenyl)pyridin-3-ylmethyl]-[2-(1H-indol-4-yloxy)-ethyl]amine hydrochloride xx) [2-(2-methyl-1H-indol-4-yloxy)ethyl]-(5-phenylpyridin-3-ylmethyl)-amine hydrochloride yy) [5-(2-fluorophenyl)pyridin-3-ylmethyl]-[2-(2-methyl-1H-indol-4-yloxy)-ethyl]amine hydrochloride zz) [5-(3-fluorophenyl)-pyridin-3-ylmethyl]-[2-(2-methyl-1H-indol-4-yloxy)-ethyl]-amine methanesulfonate aaa) [5-(2,5-difluorophenyl)-pyridin-3-ylmethyl]-[2-(2-methyl-1-H-indol-4-yloxy)-ethyl]-amine hydrochloride bbb) [5-(4-fluorophenyl)-pyridin-3-ylmethyl]-[2-(1H-indol-7-yloxy)-ethyl]-amine hydrochloride ccc) [5-(2,4-difluorophenyl)-pyridin-3-ylmethyl]-[2-(1H-indol-7-yloxy)-ethyl]-amine hydrochloride ddd) [5-(3-fluorophenyl)-pyridin-3-ylmethyl]-[2-(1H-indol-7-yloxy)-ethyl]-amine hydrochloride eee) [5-(3,4-difluorophenyl)-pyridin-3-ylmethyl]-[2-(1H-indol-4-yloxy)-ethyl]-amine hydrochloride fff) [5-(3,5-difluorophenyl)-pyridin-3-ylmethyl]-[2-(1H-indol-4-yloxy)-ethyl]-amine hydrochloride ggg) [5-(2,5-difluorophenyl)-pyridin-3-ylmethyl]-[2-(1H-indol-4-yloxy)-ethyl]-amine hydrochloride hhh) [5-(3-fluorophenyl)-pyridin-3-ylmethyl]-[2-(2-methyl-1H-indol-4-yloxy)-ethyl]-amine malonate iii) [5-(3-fluorophenyl)-pyridin-3-ylmethyl]-[2-(2-methyl-1H-indol-4-yloxy)-ethyl]-amine hemifumarate jjj) [5-(3-fluorophenyl)-pyridin-3-ylmethyl]-[2-(2-methyl-1H-indol-4-yloxy)-ethyl]-amine hemisulfate kkk) [5-(3-fluorophenyl)-pyridin-3-ylmethyl]-[2-(2-methyl-1H-indol-4-yloxy)-ethyl]-amine tartrate lll) [5-(3,5-difluorophenyl)-pyridin-3-ylmethyl]-[2-(2-methyl-1H-indol-4-yloxy)-ethyl]-amine hemifumarate mmm) [5-(2-fluorophenyl)-pyridin-3-ylmethyl]-[2-(1H-indol-4-yloxy)-ethyl]-amine dihydrochloride nnn) [2-(1H-indol-4-yloxy)-ethyl]-[5-(3,4,5-trifluorophenyl)-pyridin-3-ylmethyl]-amine dihydrochloride ooo) [2-(1H-indol-4-yloxy)-ethyl]-(5-phenyl-pyridin-3-ylmethyl)-amine dihydrochloride or a corresponding free base or another tolerable salt or solvate of the corresponding free base.

8. A compound of the formula II:

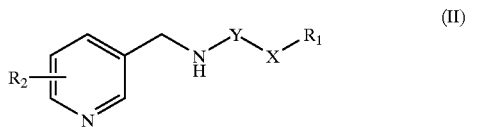
(II)

R¹ is a heterocycle radical which is quinolyl or isoquinolyl optionally substituted by at least one chlorine, or indolyl, benzothiazolyl, coumaronyl, coumarinyl, pyridyl, or carbazolyl, wherein quinolyl, isoquinolyl, indolyl, or benzothiazolyl is optionally substituted with a methyl group or an ethoxycarbonyl group and the heterocycle radical is optionally monosubstituted, disubstituted or trisubstituted by one or more of the groups -A, —OR⁴, —N(R⁴)₂, —NO₂, —CN, Hal, —COOR⁴, —CON(R⁴)₂, —COR⁴, or =O;

R² is a phenyl group which is optionally monosubstituted, disubstituted, trisubstituted, tetrasubstituted or pentasubstituted by one or more of the groups Hal, -A, —O-A, —NO₂ or —CN, or is a thienyl group which is optionally monosubstituted or disubstituted by one or more of the groups Hal, -A, —O-A, —NO₂, —CN or thienyl;

R⁴ is H or —A;

A is C₁C₆-alkyl, where 1–7 hydrogen atoms are optionally replaced by fluorine;

—X— is —O—, —S—, sulfonyl, or —C)R⁴)₂—;

—Y— is —[C(R⁴)₂]ₙ—;

Hal is F, Cl, Br or I; and n is 1, 2, 3 or 4.

9. A compound according to claim 1, wherein R¹ is quinoline-7-yl or quinoline-8-yl, where a hydrogen is optionally replaced by a chlorine atom in position 5, or indol-4-yl or indol-7-yl, where a hydrogen in position 2 of the quinolyl or indolyl is optionally replaced by a methyl group or ethoxycarbonyl group.

10. A compound according to claim 1, wherein R¹ is indol-4-yl, 2-methylindol-4-yl or quinolin-8-yl.

11. A process for the preparation of a compound of the formula I according to claim 1, comprising:

synthesizing a compound of the formula VI:

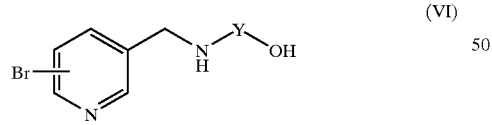
(VI)

from bromopyridin-3-ylmethanal and H₂N—Y—OH;
synthesizing a compound of the formula V:

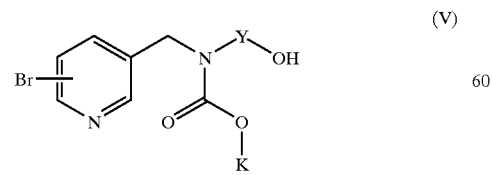
(V)

from L—CO—O—K wherein K is tert-butyl, fluoren-9-ylmethyl or benzyl, and L is Cl, N₃ or tert-butoxycarbonyloxy; and a compound of the formula VI:

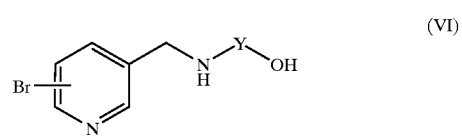
(VI)

synthesizing a compound of the formula IV:

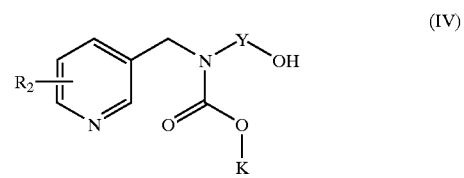
(IV)

from R²—B(OH)₂ and a compound of the formula V:

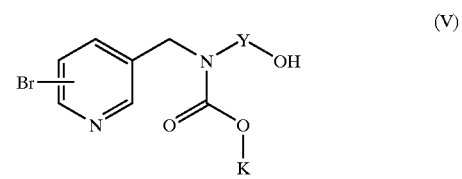
(V)

synthesizing a compound of the formula III:

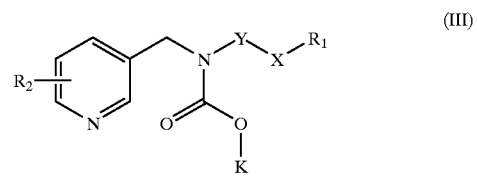
(III)

from HX—R¹ and a compound of the formula IV:

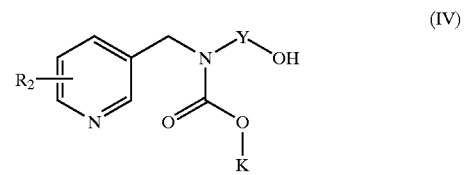
(IV)

under the conditions of the Mitsunobu reaction; or
synthesizing a compound of the formula II:

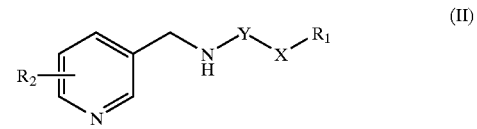
(II)

from the compound of the formula III:

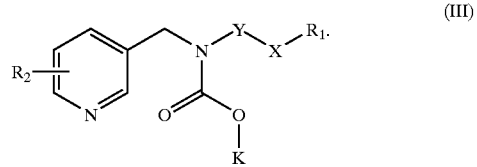
(III)

12. A compound of the formula IX:

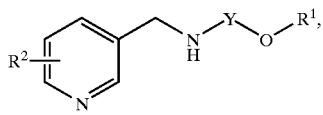
(IX)

R¹ is a heterocycle radical which is quinolyl or isoquinolyl optionally substituted by at least one chlorine, or indolyl, benzothiazolyl, coumaronyl, coumarinyl, pyridyl, or carbazolyl, wherein quinolyl, isoquinolyl, indolyl, or benzothiazolyl is optionally substituted with a methyl group or an ethoxycarbonyl group and the heterocycle radical is optionally monosubstituted, disubstituted or trisubstituted by one or more of the groups -A, —OR⁴, —N(R⁴)₂, —NO₂, —CN, Hal, —COOR⁴, —CON(R⁴)₂, —COR⁴, or =O;

R² is a phenyl group which is optionally monosubstituted, disubstituted, trisubstituted, tetrasubstituted or pentasubstituted by one or more of the groups Hal, -A, —O-A, —NO₂ or —CN, or is a thienyl group which is optionally monosubstituted or disubstituted by one or more of the groups Hal, -A, —O-A, —NO₂, —CN or thienyl;

R⁴ is H or —A;

A is $C_1C_6$-alkyl, where 1–7 hydrogen atoms are optionally replaced by fluorine;

—Y— is —[C(R⁴)₂]ₙ—;

Hal is F, Cl, Br or I; and n is 1, 2, 3 or 4.

13. A process for preparing a compound of the formula I according to claim 1, comprising one of the following:

synthesizing a compound of the formula XI:

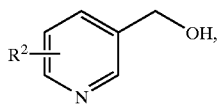
(XI)

from a compound of the formula XII:

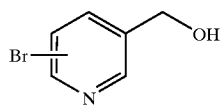
(XII)

and R²—B(OH)₂;

synthesizing a compound of the formula X:

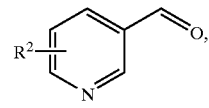
(X)

from a compound of the formula XI;
synthesizing a compound of the formula IX:

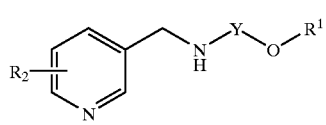
(IX)

from a compound of the formula X and R¹—O—Y—NH₂;
synthesizing a compound NH₂—Y—O—R¹, identical to a compound of the formula XIII:

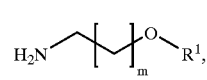
(XIII)

where m is 1, 2 or 3, from a compound of the formula XIV:

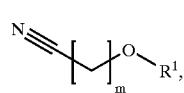
(XIV)

or
synthesizing a compound of the XIV from a compound of the formula XV:

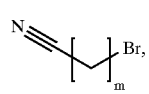
(XV)

14. A process for producing pharmaceutical preparation, comprising converting a compound according to claim 1 into a suitable dose form together with a suitable vehicle.

15. A medicament comprising a compound according to claim 1 and a pharmaceutically acceptable carrier.

16. A method of treating an illness of the central nervous system comprising administrating an effective amount of a compound according to claim 1 to a patient in need thereof.

17. A method according to claim 16, wherein the illness is schizophrenia or a psychotic anxiety state.

* * * * *

UNITED STATES PATENT AND TRADEMARK OFFICE
CERTIFICATE OF CORRECTION

PATENT NO. : 6,960,599 B2  Page 1 of 1
APPLICATION NO. : 10/311286
DATED : November 1, 2005
INVENTOR(S) : Dieter Dorsch et al.

It is certified that error appears in the above-identified patent and that said Letters Patent is hereby corrected as shown below:

Column 37, line 12, reads "[5-(4fluorophenyl)" should read -- [5-(4-fluorophenyl) --
Column 37, line 51, reads "[2-(2methyl-" should read -- [2-(2-methyl- --
Column 37, line 55 and 56, read "[2-(methylquinolin-" should read
-- [2-methylquinolin- --
Column 38, line 12, reads "(2methyl-" should read -- (2-methyl- --
Column 39, line 23, reads "—$NO_2$or" should read -- —$NO_2$ or --
Column 39, line 30, reads "—C)$R^4)_2$—" should read -- —C($R^4)_2$— --
Column 42, line 37, reads "of the XIV" should read -- of the formula XIV --

Signed and Sealed this

Eighth Day of August, 2006

JON W. DUDAS
*Director of the United States Patent and Trademark Office*